(12) United States Patent
Oyama et al.

(10) Patent No.: US 12,279,617 B2
(45) Date of Patent: Apr. 22, 2025

(54) AGRICULTURAL AND HORTICULTURAL CHEMICAL AGENT CONTAINING NEW IMIDAZOPYRIDINE-2-CARBOXAMIDE DERIVATIVE AS ACTIVE INGREDIENT

(71) Applicant: AGRO-KANESHO CO., LTD., Minato-ku (JP)

(72) Inventors: Katsuaki Oyama, Tokorozawa (JP); Kohei Ojima, Tsukubamirai (JP); Koichi Araki, Ushiku (JP); Saki Morishita, Oyama (JP); Toshiki Fukuchi, Machida (JP)

(73) Assignee: AGRO-KANESHO CO., LTD., Tokyo (JP)

( * ) Notice: Subject to any disclaimer, the term of this patent is extended or adjusted under 35 U.S.C. 154(b) by 724 days.

(21) Appl. No.: 17/618,285

(22) PCT Filed: Jun. 12, 2020

(86) PCT No.: PCT/JP2020/023192
§ 371 (c)(1),
(2) Date: Dec. 10, 2021

(87) PCT Pub. No.: WO2020/251013
PCT Pub. Date: Dec. 17, 2020

(65) Prior Publication Data
US 2022/0330550 A1    Oct. 20, 2022

(30) Foreign Application Priority Data
Jun. 13, 2019 (JP) ................................ 2019-110238

(51) Int. Cl.
*A01N 43/90* (2006.01)
*A01P 7/02* (2006.01)
*C07D 471/04* (2006.01)

(52) U.S. Cl.
CPC ................ *A01N 43/90* (2013.01); *A01P 7/02* (2021.08); *C07D 471/04* (2013.01)

(58) Field of Classification Search
CPC .. C07D 471/04; C07D 471/02; C07D 471/00; A01N 43/90; A01P 7/02; A01P 7/00; A01P 7/04; A61K 31/437; A61K 31/444
See application file for complete search history.

(56) References Cited

U.S. PATENT DOCUMENTS

| | | |
|---|---|---|
| 2015/0189880 A1 | 7/2015 | Maehata et al. |
| 2015/0336881 A1 | 11/2015 | Maehata et al. |
| 2015/0336895 A1 | 11/2015 | Maehata et al. |
| 2016/0280668 A1 | 9/2016 | Hallenbach et al. |
| 2018/0077934 A1 | 3/2018 | Kojima et al. |
| 2018/0132482 A1 | 5/2018 | Furuya et al. |

FOREIGN PATENT DOCUMENTS

| | | |
|---|---|---|
| JP | 2018-24660 A | 2/2018 |
| JP | 2019-6740 A | 1/2019 |
| WO | WO 2013/191041 A1 | 12/2013 |
| WO | WO 2014/002754 A1 | 1/2014 |
| WO | WO 2014/021468 A1 | 2/2014 |
| WO | WO 2015/067648 A1 | 5/2015 |
| WO | WO 2015/117912 A1 | 8/2015 |
| WO | WO 2016/182021 A1 | 11/2016 |

OTHER PUBLICATIONS

Casida, J. E. "Pest Toxicology: The Primary Mechanisms of Pesticide Action" Chemical Research in Toxicology 2009, vol. 22, pp. 609-612. (Year: 2009).*
English language machine translation of JP2018024660A (translated Sep. 19, 2024). (Year: 2018).*
English language machine translation of JP2019006740A1 (translated Sep. 20, 2024). (Year: 2019).*
International Search Report issued on Aug. 11, 2020 in PCT/JP2020/023192 filed Jun. 12, 2020, 2 pages.

* cited by examiner

*Primary Examiner* — Eric Olson
*Assistant Examiner* — Benjamin M Brandsen
(74) *Attorney, Agent, or Firm* — Oblon, McClelland, Maier & Neustadt, L.L.P.

(57) ABSTRACT

A compound may be used as an active ingredient of an agricultural and horticultural chemical agent, in particular, an agricultural and horticultural pest control agent such as an agricultural and horticultural insecticide or an agricultural and horticultural mite control agent. Such a compound is an imidazopyridine-2-carboxamide derivative or its N-oxide or salt of formula (1):

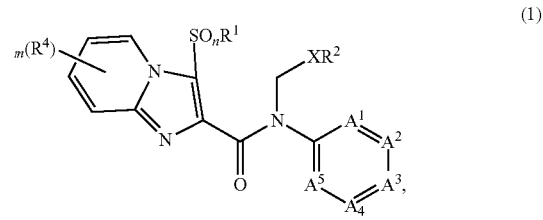

in the formula, $R^1$ and $R^2$ are, for example, $C_{1-3}$ alkyl groups, X is, for example, O or S, $A^1$, $A^2$, $A^3$, $A^4$, and $A^5$ are each independently N or C—$R^3$, $R^3$ is, for example, H or a $C_{1-3}$ haloalkyl group, and $R^4$ is, for example, a $C_{1-3}$ alkyl group or a $C_{1-3}$ haloalkyl group.

20 Claims, No Drawings

AGRICULTURAL AND HORTICULTURAL CHEMICAL AGENT CONTAINING NEW IMIDAZOPYRIDINE-2-CARBOXAMIDE DERIVATIVE AS ACTIVE INGREDIENT

CROSS-REFERENCE TO RELATED APPLICATIONS

The present application is the national stage of international application PCT/JP2020/023192, filed on Jun. 12, 2020, and claims the benefit of the filing date of Japanese Appl. No. 2019-110238, filed on Jun. 13, 2019, the content of each of which is incorporated by reference.

TECHNICAL FIELD

The present invention relates to a new imidazopyridine-2-carboxamide compound and a method of using the compound as an active ingredient of an agricultural and horticultural chemical agent, in particular, as an agricultural and horticultural insecticide.

BACKGROUND ART

In the field of agriculture and horticulture, plant pest control agents for the purpose of controlling various pests have been developed and applied to practical uses. However, conventionally used agricultural and horticultural insecticides are not always satisfied in, for example, insecticidal effect or residual efficacy and also could not be said that the requirements for, for example, reductions in the number of applications and in the amount of the agent in application have been satisfied.

In addition, the appearance of various mites which have acquired resistance to conventionally used miticides has also become a problem.

It is eagerly desired to develop a new insecticide that shows a sufficient controlling effect with a low dose also on various pests which have acquired resistance to conventionally used agricultural and horticultural insecticides and that is less harmful to the environment.

New miticides for responding to these demands have been variously proposed, but they do not necessarily meet the above demands.

As imidazopyridine-2-carboxamide derivatives that are similar to the present invention, the following compounds A and B are disclosed.

Patent Literature 1 discloses compounds including the following compound A. However, Patent Literature 1 does not disclose any N-alkyloxy group and any N-alkylthio group, which groups are possessed by the present invention compound at all.

Patent Literature 1: Compound A

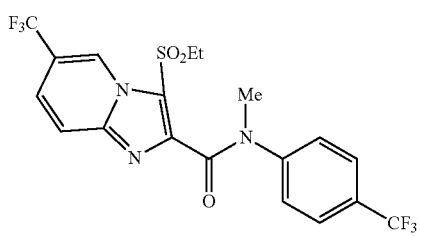

Patent Literature 2 discloses compounds including the following compound B, but the acid site thereof is limited to a pyridine ring, and Patent Literature 2 does not disclose any imidazopyridine ring at all.

Patent Literature 2: Compound B

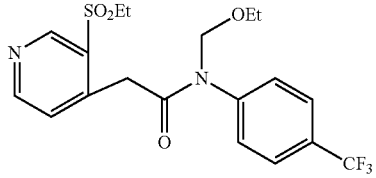

The present inventors diligently studied and, as a result, found that the present compound has a significantly high insecticidal activity compared to the compounds A and B. Such an improvement in the activity was completely unexpected and was first revealed by the experiments carried out by the present inventors.

On the other hand, Patent Literatures encompassing the following compounds as carboxamide derivatives having an acid site of an aromatic ring or an aromatic heterocyclic ring and including an N-alkyl group have been disclosed.

Patent Literature 3

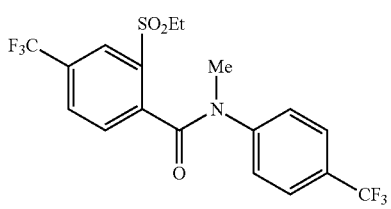

Patent Literature 4

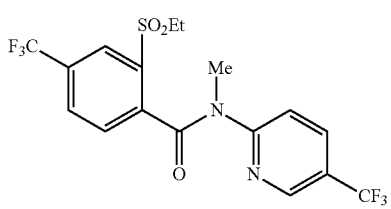

Patent Literature 5

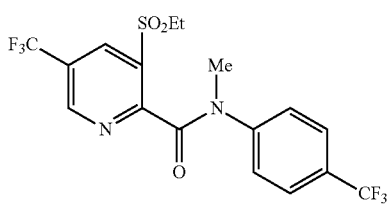

Patent Literature 6

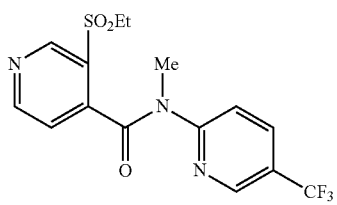

-continued

Patent Literature 7

However, these compounds are not compounds having an N-alkoxy group or an N-alkylthio group. In addition, the acid side portion also does not include an imidazopyridine ring.

CITATION LIST

Patent Literatures

Patent Literature 1: JP-A-2018-024660
Patent Literature 2: JP-A-2019-006740
Patent Literature 3: WO 2013/191041
Patent Literature 4: WO 2014/002754
Patent Literature 5: WO 2014/021468
Patent Literature 6: WO 2015/067648
Patent Literature 7: WO 2015/117912

SUMMARY OF INVENTION

Subject to be Attained by the Present Invention

It is an object of the present invention to provide a new substance useful for controlling various pests in the field of agriculture and horticulture. In particular, the present invention is to provide a substance which exhibits a high controlling effect also on various pests having resistance to conventional insect pest control agents; which further exhibits the effect with a low dose; and which has a high safety with reduced problems of residual toxicity and environmental problems such as environmental pollution.

Means for Attaining the Subject

Accordingly, the present inventors have diligently studied to attaining the above subject and, as a result, have found that an imidazopyridine-2-carboxamide derivative represented by the following formula (1), which is a new compound which was not described in the literatures, is useful as agricultural and horticultural chemical agents which can meet the above demands, in particular, which are useful as agricultural and horticultural insecticides, and thus the present invention has been accomplished.

That is, the present invention relates to an imidazopyridine-2-carboxamide derivative represented by the following formula (1):

(1)

[in the formula,
$R^1$ represents a $C_{1-6}$ alkyl group or a $C_{1-6}$ haloalkyl group;
$R^2$ represents a hydrogen atom, a $C_{1-6}$ alkyl group, or a $C_{1-6}$ haloalkyl group;
X represents an oxygen atom, a sulfur atom, or —$SO_2$—;
$A^1$, $A^2$, $A^3$, $A^4$, and $A^5$ each independently represents a nitrogen atom or C—$R^3$, provided that two of $A^1$, $A^2$, $A^3$, $A^4$, and $A^5$ are not nitrogen atoms at the same time, and at least one of $A^1$, $A^2$, $A^3$, $A^4$, and $A^5$ is C—$R^3$,
$R^3$s may be the same or different from each other, and each $R^3$ represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a $C_{3-6}$ alkenyloxy group, a $C_{3-6}$ alkynyloxy group, a $C_{1-6}$ haloalkoxy group, a $C_{3-6}$ haloalkenyloxy group, a $C_{3-6}$ haloalkynyloxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a nitro group, a cyano group, a phenyl group optionally substituted with one to four $R^5$s, a phenoxy group optionally substituted with one to four $R^6$s, or a triazolyl group substituted with one or two $R^7$s, or when two $R^3$s are substituted on adjacent two carbon atoms, the two $R^3$s may form a saturated or unsaturated 5- or 6-membered ring together with such adjacent two carbon atoms to which the $R^3$s are respectively bound, and
$R^5$, $R^6$, and $R^7$ each independently represents a halogen atom, a $C_{1-6}$ alkyl group, a $C_{1-6}$ haloalkyl group, a $C_{3-8}$ cycloalkyl group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, or a $C_{1-6}$ haloalkylsulfonyl group;
$R^4$s may be the same or different from each other and each represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a nitro group, or a cyano group;
n represents an integer of 0 to 2; and
m represents an integer of 0 to 4],
or its N-oxide or salt, and the present invention also relates to a use thereof and a manufacturing method thereof.

Effect of Invention

The compound of the present invention exhibits an excellent effect as an agricultural and horticultural chemical agent, in particular, as an agricultural and horticultural insecticide. In addition, the present compound provides an effect on pests that parasitize pet animals, such as dogs and cats, or livestock, such as cows and sheep.

DESCRIPTION OF EMBODIMENTS

In the definition of the present compound of the present invention represented by the formula (1), the term "halogen atom" represents a chlorine atom, a bromine atom, a iodine atom, or a fluorine atom, the term "$C_{1-6}$ alkyl group" represents a linear or branched chain alkyl group having 1 to 6, preferably 1 to 3 carbon atoms, such as a methyl group, an ethyl group, an n-propyl group, an i-propyl group, an n-butyl group, an i-butyl group, an s-butyl group, a t-butyl group, an n-pentyl group, an isopentyl group, a neopentyl group, a tert-pentyl group, an n-hexyl group, and an isohexyl group, the term "$C_{1-6}$ haloalkyl group" represents the above prescribed linear or branched chain alkyl group having 1 to 6 carbon atoms substituted with the same or different one or more, preferably 1 to 3, halogen atoms, and the term "$C_{3-8}$ cycloalkyl group" represents a cycloalkyl group having 3 to 8, preferably 3 to 6 carbon atoms, such as cyclopropyl, cyclobutyl, cyclopentyl, cyclohexyl, and cyclooctyl groups.

Examples of the term "$C_{1-6}$ haloalkyl group" include the above prescribed linear or branched chain alkyl groups having 1 to 6 carbon atoms substituted with 1 to 13, preferably 1 to 9 halogen atoms, such as a fluoromethyl group, a chloromethyl group, a difluoromethyl group, a trifluoromethyl group, a chlorodifluoromethyl group, a bromodifluoromethyl group, a dichlorofluoromethyl group, a 1-fluoroethyl group, a 2-fluoroethyl group, a 2-chloroethyl group, a 2-bromoethyl group, a 2-iodoethyl group, a 2,2,2-trifluoroethyl group, a 2,2,2-trichloroethyl group, a pentafluoroethyl group, a 1-fluoroisopropyl group, a 3-fluoropropyl group, a 3-chloropropyl group, a 3-bromopropyl group, a heptafluoropropyl group, a 4-fluorobutyl group, a 4-chlorobutyl group, a nonafluorobutyl group, a 5,5,5-trifluoropentyl group, a 5-chloropentyl group, an undecafluoropentyl group, a 6,6,6-trifluorohexyl group, a 6-chlorohexyl group, and a tridecafluorohexyl group.

Examples of the term "$C_{1-6}$ alkoxy group" include linear or branched chain alkoxy groups having 1 to 6, preferably 1 to 3 carbon atoms, such as a methoxy group, an ethoxy group, an n-propoxy group, an isopropoxy group, an n-butoxy group, a sec-butoxy group, a tert-butoxy group, an n-pentoxy group, and an n-hexyloxy group.

Examples of the term "$C_{1-6}$ haloalkoxy group" include the above prescribed linear or branched chain alkoxy groups having 1 to 6 carbon atoms substituted with 1 to 9 halogen atoms, such as a fluoromethoxy group, a dichloromethoxy group, a trichloromethoxy group, a difluoromethoxy group, a trifluoromethoxy group, a chlorodifluoromethoxy group, a bromodifluoromethoxy group, a dichlorofluoromethoxy group, a 1-fluoroethoxy group, a 2-fluoroethoxy group, a 2-chloroethoxy group, a 2-bromoethoxy group, a 2-iodoethoxy group, a 2,2,2-trifluoroethoxy group, a 2,2,2-trichloroethoxy group, a pentafluoroethoxy group, a 1-fluoroisopropoxy group, a 3-fluoropropoxy group, a 3-chloropropoxy group, a 3-bromopropoxy group, a 4-fluorobutoxy group, and a 4-chlorobutoxy group.

Examples of the term "$C_{3-6}$ alkenyloxy group" include linear or branched chain alkenyloxy groups having 3 to 6, preferably 3 to 5 carbon atoms and having at least one double bond at an arbitrary position, such as an allyloxy group, an isopropenyloxy group, a 2-butenyloxy group, a 3-butenyloxy group, a 1-methyl-2-propenyloxy group, a 2-pentenyloxy group, a 3-pentenyloxy group, a 4-pentenyloxy group, a 1,1-dimethyl-2-propenyloxy group, a 1-ethyl-2-propenyloxy group, a 1-methyl-2-butenyloxy group, a 1-methyl-3-butenyloxy group, a 2-hexenyloxy group, a 3-hexenyloxy group, a 4-hexenyloxy group, a 5-hexenyloxy group, a 1,1-dimethyl-2-butenyloxy group, and a 1,1-dimethyl-3-butenyloxy group.

Examples of the term "$C_{3-6}$ haloalkenyloxy group" include the above prescribed linear or branched chain alkenyloxy groups having 3 to 6 carbon atoms, having at least one double bond at an arbitrary position and further being substituted with 1 to 13, preferably 1 to 7 halogen atoms, such as a 3-chloro-2-propenyloxy group, a 3,3-difluoro-2-allyloxy group, a 3,3-dichloro-2-allyloxy group, a 4,4,4-trifluoro-2-butenyloxy group, a 4,4,4-trifluoro-3-butenyloxy group, a 5-chloro-3-pentenyloxy group, and a 6-fluoro-2-hexenyloxy group.

Examples of the term "$C_{3-6}$ alkynyloxy group" include linear or branched chain alkynyloxy groups having 3 to 6, preferably 3 to 5 carbon atoms and having at least one triple bond at an arbitrary position, such as a 2-propynyloxy group, a 1-methyl-2-propynyloxy group, a 1,1-dimethyl-2-propynyloxy group, a 1-butynyloxy group, a 2-butynyloxy group, a 3-butynyloxy group, a 1-pentynyloxy group, a 2-pentynyloxy group, a 3-pentynyloxy group, a 4-pentynyloxy group, a 1-methyl-2-butynyloxy group, a 1-methyl-3-butynyloxy group, a 1,1-dimethyl-2-butynyloxy group, a 1,1-dimethyl-3-butynyloxy group, a 1-methyl-3-pentynyloxy group, and a 1-methyl-4-pentynyloxy group.

Examples of the term "$C_{3-6}$ haloalkynyloxy group" include the above prescribed linear or branched chain alkynyloxy groups having 3 to 6 carbon atoms, having at least one triple bond at an arbitrary position and being substituted with 1 to 9, preferably 1 to 6 halogen atoms, such as a 4,4,4-trifluoro-2-butynyloxy group, a 5,5,5-trifluoro-3-pentynyloxy group, a 1-methyl-3,3,3-trifluoro-2-butynyloxy group, and a 1-methyl-5,5,5-trifluoro-2-pentynyloxy group.

Examples of the term "$C_{1-6}$ alkylthio group" include linear or branched chain alkylthio groups having 1 to 6, preferably 1 to 3 carbon atoms, such as a methylthio group, an ethylthio group, an n-propylthio group, an isopropylthio group, an n-butylthio group, a sec-butylthio group, a tert-butylthio group, an n-pentylthio group, and an n-hexylthio group.

Examples of the term "$C_{1-6}$ alkylsulfinyl group" include linear or branched chain alkylsulfinyl groups having 1 to 6, preferably 1 to 3 carbon atoms, such as a methylsulfinyl group, an ethylsulfinyl group, an n-propylsulfinyl group, an isopropylsulfinyl group, an n-butylsulfinyl group, a sec-butylsulfinyl group, a tert-butylsulfinyl group, an n-pentylsulfinyl group, and an n-hexylsulfinyl group.

Examples of the term "$C_{1-6}$ alkylsulfonyl group" include linear or branched chain alkylsulfonyl groups having 1 to 6, preferably 1 to 3 carbon atoms, such as a methylsulfonyl group, an ethylsulfonyl group, an n-propylsulfonyl group, an isopropylsulfonyl group, an n-butylsulfonyl group, a sec-butylsulfonyl group, a tert-butylsulfonyl group, an n-pentylsulfonyl group, and an n-hexylsulfonyl group.

Examples of the term "$C_{1-6}$ haloalkylthio group" include linear or branched chain alkylthio groups having 1 to 6, preferably 1 to 3 carbon atoms substituted with 1 to 13, preferably 1 to 9 halogen atoms, such as a difluoromethylthio group, a trifluoromethylthio group, a monochloromethylthio group, a dichloromethylthio group, a trichloromethylthio group, a monobromomethylthio group, a dibromomethylthio group, a tribromomethylthio group, a 1-fluoroethylthio group, a 2-fluoroethylthio group, a 2,2-difluoroethylthio group, a 2,2,2-trifluoroethylthio group, a 2-chloro-2,2-difluoroethylthio group, a 1-chloroethylthio group, a 2-chloroethylthio group, a 2,2,-dichloroethylthio group, a 2,2,2-trichloroethylthio group, a 2-bromoethylthio group, a 2,2-dibromoethylthio group, a 2,2,2-tribromoethylthio group, a pentafluoroethylthio group, a 3-fluoropropylthio group, a 3-chloropropylthio group, a 3-bromopropylthio group, a 1,3-difluoro-2-propylthio group, a 3,3,3-trifluoropropylthio group, a 1,3-dichloro-2-propylthio group, a 1,1,1-trifluoro-2-propylthio group, a 1-chloro-3-fluoro-2-propylthio group, a 1,1,1,3,3,3-hexafluoro-2-propylthio group, a 1,1,1,3,3,3-hexafluoro-2-chloro-2-propylthio group, a 2,2,3,3,3-pentafluoropropylthio group, a heptafluoroisopropylthio group, a heptafluoro-n-propylthio group, a 4-fluorobutylthio group, a 4,4,4-trifluorobutylthio group, a nonafluoro-n-butylthio group, and a nonafluoro-2-butylthio group.

Examples of the term "$C_{1-6}$ haloalkylsulfinyl group" 10 include linear or branched chain alkylsulfinyl groups having 1 to 6, preferably 1 to 3 carbon atoms substituted with 1 to 13, preferably 1 to 9 halogen atoms, such as a difluoromethylsulfinyl group, a trifluoromethylsulfinyl group, a dichloromethylsulfinyl group, a trichloromethylsulfinyl group, a monobromomethylsulfinyl group, a dibromomethylsulfinyl group, a tribromomethylsulfinyl group, a 1-fluoroethylsulfinyl group, a 2-fluoroethylsulfinyl group, a 2,2-difluoroethylsulfinyl group, a 2,2,2-trifluoroethylsulfinyl group, a 2-chloro-2,2-difluoroethylsulfinyl group, a 1-chloroethylsulfinyl group, a 2-chloroethylsulfinyl group, a 2,2,-dichloroethylsulfinyl group, a 2,2,2-trichloroethylsulfinyl group, a 2-bromoethylsulfinyl group, a 2,2-dibromoethylsulfinyl group, a 2,2,2-tribromoethylsulfinyl group, a pentafluoroethylsulfinyl group, a 3-fluoropropylsulfinyl group, a 3-chloropropylsulfinyl group, a 3-bromopropylsulfinyl group, a 1,3-difluoro-2-propylsulfinyl group, a 3,3,3-trifluoropropylsulfinyl group, a 1,3-dichloro-2-propylsulfinyl group, a 1,1,1-trifluoro-2-propylsulfinyl group, a 1-chloro-3-fluoro-2-propylsulfinyl group, a 1,1,1,3,3,3-hexafluoro-2-propylsulfinyl group, a 1,1,1,3,3,3-hexafluoro-2-chloro-2-propylsulfinyl group, a 2,2,3,3,3-pentafluoropropylsulfinyl group, a heptafluoroisopropylsulfinyl group, a heptafluoro-n-propylsulfinyl group, a 4-fluorobutylsulfinyl group, a 4,4,4-trifluorobutylsulfinyl group, a nonafluoro-n-butylsulfinyl group, and a nonafluoro-2-butylsulfinyl group.

Examples of the term "$C_{1-6}$ haloalkylsulfonyl group" include linear or branched chain alkylsulfonyl groups having 1 to 6, preferably 1 to 3, carbon atoms substituted with 1 to 13, preferably 1 to 9, halogen atoms, such as a difluoromethylsulfonyl group, a trifluoromethylsulfonyl group, a dichloromethylsulfonyl group, a trichloromethylsulfonyl group, a monobromomethylsulfonyl group, a dibromomethylsulfonyl group, a tribromomethylsulfonyl group, a 1-fluoroethylsulfonyl group, a 2-fluoroethylsulfonyl group, a 2,2-difluoroethylsulfonyl group, a 2,2,2-trifluoroethylsulfonyl group, a 2-chloro-2,2-difluoroethylsulfonyl group, a 1-chloroethylsulfonyl group, a 2-chloroethylsulfonyl group, a 2,2,-dichloroethylsulfonyl group, a 2,2,2-trichloroethylsulfonyl group, a 2-bromoethylsulfonyl group, a 2,2-dibromoethylsulfonyl group, a 2,2,2-tribromoethylsulfonyl group, a pentafluoroethylsulfonyl group, a 3-fluoropropylsulfonyl group, a 3-chloropropylsulfonyl group, a 3-bromopropylsulfonyl group, a 1,3-difluoro-2-propylsulfonyl group, a 3,3,3-trifluoropropylsulfonyl group, a 1,3-dichloro-2-propylsulfonyl group, a 1,1,1-trifluoro-2-propylsulfonyl group, a 1-chloro-3-fluoro-2-propylsulfonyl group, a 1,1,1,3,3,3-hexafluoro-2-propylsulfonyl group, a 1,1,1,3,3,3-hexafluoro-2-chloro-2-propylsulfonyl group, a 2,2,3,3,3-pentafluoropropylsulfonyl group, a heptafluoroisopropylsulfonyl group, a heptafluoro-n-propylsulfonyl group, a 4-fluorobutylsulfonyl group, a 4,4,4-trifluorobutylsulfonyl group, a nonafluoro-n-butylsulfonyl group, and a nonafluoro-2-butylsulfonyl group.

Examples of the salt of the imidazopyridine-2-carboxamide derivative represented by the formula (1) of the present invention include inorganic acid salts, such as hydrochloride, sulfate, nitrate, and phosphate, and organic acid salts, such as acetate, fumarate, maleate, oxalate, methanesulfonate, benzenesulfonate, and p-toluenesulfonate.

The imidazopyridine-2-carboxamide derivative represented by the formula (1) of the present invention may include one or more asymmetric centers in its structural formula, and two or more optical isomers and diastereomers may be present. The present invention encompasses these optical isomers and a mixture containing them in any arbitrary proportions. In addition, in the imidazopyridine-2-carboxamide derivative represented by the formula (1) of the present invention, two geometrical isomers derived from a carbon-carbon double bond may be present, and the present invention encompasses these geometrical isomers and a mixture containing them in any arbitrary proportions.

Among the compounds of the present invention, preferred are those compounds in which $R^2$ is a $C_{1-3}$ alkyl group or a $C_{1-3}$ haloalkyl group, and further preferred are those compounds in which $R^2$ is a methyl group.

Among those compounds of the present invention, preferred are compounds in which $R^1$ is a $C_{1-3}$ alkyl group or a $C_{1-3}$ haloalkyl group, and further preferred are those compounds in which $R^1$ is a $C_{1-3}$ alkyl group.

Among the compounds of the present invention, preferred are those compounds in which $R^3$ and $R^4$ are $C_{1-3}$ haloalkyl groups, and further preferred are those compounds in which $R^3$ and $R^4$ are $C_{1-3}$ alkyl groups.

A typical method for manufacturing the new imidazopyridine-2-carboxamide derivative represented by the formula (1) of the present invention will now be described, but the scope of the present invention is not limited thereto.

Reaction formula 1

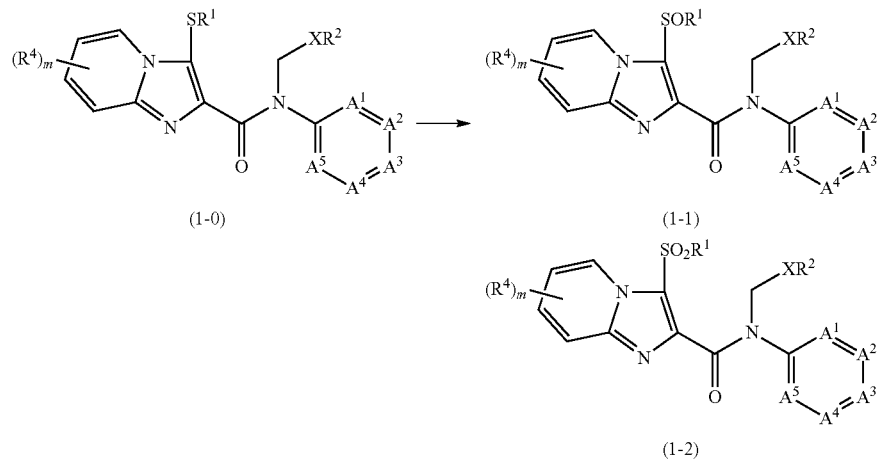

[In the formula, $R^1$, $R^2$, $R^3$, $R^4$, $A^1$, $A^2$, $A^3$, $A^4$, $A^5$, X, and m are as defined above].

In the method shown in the reaction formula 1, the imidazopyridine-2-carboxamide derivatives (1-1) and (1-2) represented by the formula (1) are manufactured by oxidation reaction of the imidazopyridine-2-carboxamide derivative represented by the formula (1-0).

As the solvent to be used in the oxidation reaction of the compound of the formula (1-0), a solvent which is inert to the reaction can be widely used, and examples thereof include aliphatic or alicyclic hydrocarbon solvents, such as hexane, cyclohexane, and heptane; aromatic hydrocarbon solvents, such as benzene, chlorobenzene, toluene, and xylene; halogenated hydrocarbon solvents, such as methylene chloride, 1,2-dichloroethane, and chloroform; alcoholic solvents, such as methanol and ethanol; ester solvents, such as methyl acetate and ethyl acetate; ketone solvents, such as acetone and methyl ethyl ketone; amide solvents, such as N,N-dimethylformamide; nitrile solvents, such as acetonitrile and propionitrile; non-protonic polar solvents, such as N-methylpyrrolidone and N,N'-dimethylimidazolinone; and acetic acid. These solvents can be used alone or as a mixture of two or more thereof as needed.

The oxidizing agent to be used in the oxidation reaction of the formula (1-0) is, for example, m-chloroperbenzoic acid, sodium periodate, or hydrogen peroxide.

Such an oxidizing agent can be usually used in an amount of 1 to 3 equivalents, preferably 1 to 2.5 equivalents, with respect to the imidazopyridine-2-carboxamide derivative represented by the formula (1-0).

The reaction can be performed usually within a temperature range of −78° C. to the boiling point of the used solvent, and the reaction is preferably performed at a temperature from 0° C. to room temperature.

The reaction time varies depending on the reaction temperature, etc., and although it cannot be said unconditionally, the reaction is usually completed in about 0.5 to 24 hours.

The target compounds obtained by each of the above reactions can be easily isolated from a reaction mixture by an isolation method that is generally performed, such as organic solvent extraction, chromatography, a recrystallization method, or a distillation method and can be further purified by a general purification method.

Reaction formula 2

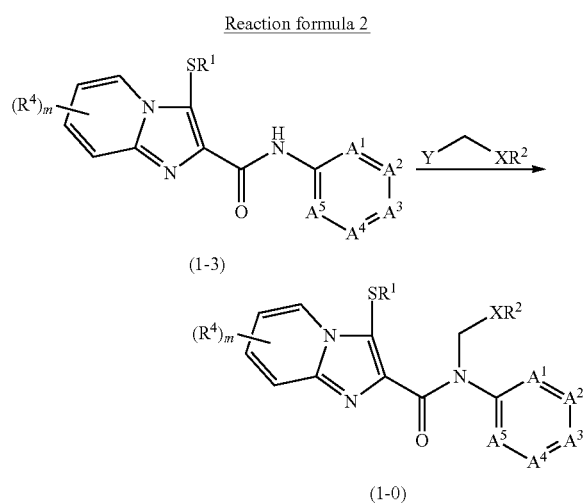

(1-3)

(1-0)

[in the formula, $R^1$, $R^2$, $R^3$, $R^4$, $A^1$, $A^2$, $A^3$, $A^4$, $A^5$, X, and m are as defined above, and Y represents a chlorine atom, a bromine atom, an iodine atom, a methanesulfonyloxy group, or a trifluoromethanesulfonyloxy group].

In the method shown in the reaction formula 2, an imidazopyridine-2-carboxamide derivative represented by the formula (1-3) and a halogenated ether derivative or a halogenated thioether derivative represented by $YCH_2XR^2$ are allowed to react with each other in a solvent in the presence of a base according to the method described in Bioorganic Medicinal Chemistry Letters, 18 (20), 5537-5540 (2008) to manufacture a compound of the formula (1-0).

As the solvent to be used in the reaction shown in the reaction formula 2, a known solvent can be widely used as long as the solvent is inert to the reaction, and examples thereof can include ether solvents, such as diethyl ether, tetrahydrofuran, and 1,4-dioxane; amide solvents, such as N,N-dimethylformamide; and solvents, such as dimethyl sulfoxide, N-methylpyrrolidone, and N,N'-dimethylimidazolinone. These solvents can be used alone or as a mixture of two or more thereof as needed.

As the base to be used in the reaction, a known inorganic base or organic base can be used, and examples thereof can include alkali metal hydrides, such as sodium hydride and potassium hydride; alkali metal carbonates, such as sodium carbonate and potassium carbonate; alkali metal hydroxides, such as sodium hydroxide, potassium hydroxide, and lithium hydroxide; alkali metal alkoxides, such as potassium t-butoxide; and organic bases, such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), and 1,8-diazabicyclo[5.4.0]-7-undecene (DBU). Preferred are alkali metal hydrides, alkali metal carbonates, and alkali metal hydroxides, and further preferred are sodium hydride and potassium carbonate.

The amount of the base used can be usually 1 to 3 equivalents, preferably 1 to 2.5 equivalents, based on 1 mole of the compound of the formula (1-3).

The reaction is preferably performed at a temperature from 0° C. to the boiling point of the used solvent, more preferably at a temperature from 0° C. to 80° C.

The reaction is usually completed in a reaction time of about 0.5 to 24 hours.

After the completion of the reaction, it is sufficient that the object compound is isolated from the reaction system containing the object compound by a usual method and the object compound can be purified by, for example, recrystallization or column chromatography as needed, so as to produce the object compound. Thus, the object compound can be manufactured. Alternatively, the object can be subjected to the subsequent process without isolating the object compound from the reaction system.

The imidazopyridine-2-carboxamide derivative represented by the general formula (1-3) to be used in the present reaction can be synthesized, for example, according to the method described in JP-A-2018-24672.

Typical examples of the imidazopyridine-2-carboxamide derivative compound represented by the formula (1) are shown in Table 1, but the scope of the present invention is not limited to them.

Incidentally, the physical properties in the table show the nature or the melting point (° C.), "n" represents normal, "i" represents iso, "Me" represents a methyl group, "Et" represents an ethyl group, and "Pr" represents a propyl group.

General formula (1)

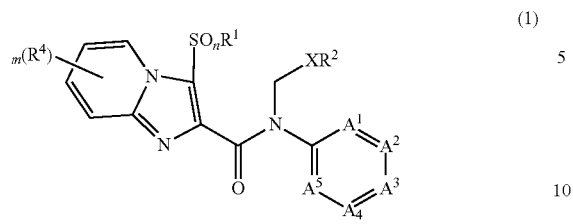

TABLE 1

| Compound No. | $R^1$ | $R^2$ | $(R^4)_m$ | $A^1$ | $A^2$ | $A^3$ | $A^4$ | $A^5$ | X | n | Melting point |
|---|---|---|---|---|---|---|---|---|---|---|---|
| A-1 | Me | Et | 6-$CF_3$ | CH | CH | $CCF_3$ | CH | CH | O | 0 | oil |
| A-2 | Me | Et | 6-$CF_3$ | CH | CH | $CCF_3$ | CH | CH | O | 1 | 136-141 |
| A-3 | Me | Et | 6-$CF_3$ | CH | CH | $CCF_3$ | CH | CH | O | 2 | 121-122 |
| A-4 | Et | Et | 6-$CF_3$ | CH | CH | $CCF_3$ | CH | CH | O | 0 | oil |
| A-5 | Et | Et | 6-$CF_3$ | CH | CH | $CCF_3$ | CH | CH | O | 1 | 135-136 |
| A-6 | Et | Et | 6-$CF_3$ | CH | CH | $CCF_3$ | CH | CH | O | 2 | 124-126 |
| A-7 | nPr | Et | 6-$CF_3$ | CH | CH | $CCF_3$ | CH | CH | O | 0 | oil |
| A-8 | nPr | Et | 6-$CF_3$ | CH | CH | $CCF_3$ | CH | CH | O | 1 | 116-117 |
| A-9 | nPr | Et | 6-$CF_3$ | CH | CH | $CCF_3$ | CH | CH | O | 2 | 120-122 |
| A-10 | iPr | Et | 6-$CF_3$ | CH | CH | $CCF_3$ | CH | CH | O | 0 | oil |
| A-11 | iPr | Et | 6-$CF_3$ | CH | CH | $CCF_3$ | CH | CH | O | 1 | 106-111 |
| A-12 | iPr | Et | 6-$CF_3$ | CH | CH | $CCF_3$ | CH | CH | O | 2 | |
| A-13 | Et | Me | 6-$CF_3$ | CH | CH | $CCF_3$ | CH | CH | O | 0 | 103-105 |
| A-14 | Et | Me | 6-$CF_3$ | CH | CH | $CCF_3$ | CH | CH | O | 1 | 147-149 |
| A-15 | Et | Me | 6-$CF_3$ | CH | CH | $CCF_3$ | CH | CH | O | 2 | 165-166 |
| A-16 | Et | Et | 5-$CF_3$ | CH | CH | $CCF_3$ | CH | CH | O | 0 | oil |
| A-17 | Et | Et | 5-$CF_3$ | CH | CH | $CCF_3$ | CH | CH | O | 1 | |
| A-18 | Et | Et | 5-$CF_3$ | CH | CH | $CCF_3$ | CH | CH | O | 2 | 154-157 |
| A-19 | Et | Et | 7-$CF_3$ | CH | CH | $CCF_3$ | CH | CH | O | 0 | 66-74 |
| A-20 | Et | Et | 7-$CF_3$ | CH | CH | $CCF_3$ | CH | CH | O | 1 | 92-94 |
| A-21 | Et | Et | 7-$CF_3$ | CH | CH | $CCF_3$ | CH | CH | O | 2 | oil |
| A-22 | Et | Et | 8-$CF_3$ | CH | CH | $CCF_3$ | CH | CH | O | 0 | oil |
| A-23 | Et | Et | 8-$CF_3$ | CH | CH | $CCF_3$ | CH | CH | O | 1 | |
| A-24 | Et | Et | 8-$CF_3$ | CH | CH | $CCF_3$ | CH | CH | O | 2 | oil |
| A-25 | Et | Et | 6-Cl | CH | CH | $CCF_3$ | CH | CH | O | 0 | oil |
| A-26 | Et | Et | 6-Cl | CH | CH | $CCF_3$ | CH | CH | O | 1 | |
| A-27 | Et | Et | 6-Cl | CH | CH | $CCF_3$ | CH | CH | O | 2 | 96-100 |
| A-28 | Et | Et | 6-Me | CH | CH | $CCF_3$ | CH | CH | O | 0 | oil |
| A-29 | Et | Et | 6-Me | CH | CH | $CCF_3$ | CH | CH | O | 1 | oil |
| A-30 | Et | Et | 6-Me | CH | CH | $CCF_3$ | CH | CH | O | 2 | 81-87 |
| A-31 | Et | Et | 6-$CF_3$ | $CCF_3$ | CH | CH | CH | CH | O | 0 | oil |
| A-32 | Et | Et | 6-$CF_3$ | $CCF_3$ | CH | CH | CH | CH | O | 1 | |
| A-33 | Et | Et | 6-$CF_3$ | $CCF_3$ | CH | CH | CH | CH | O | 2 | oil |
| A-34 | Et | Et | 6-$CF_3$ | CH | $CCF_3$ | CH | CH | CH | O | 0 | oil |
| A-35 | Et | Et | 6-$CF_3$ | CH | $CCF_3$ | CH | CH | CH | O | 1 | |
| A-36 | Et | Et | 6-$CF_3$ | CH | $CCF_3$ | CH | CH | CH | O | 2 | 137-140 |
| A-37 | Et | Et | 6-$CF_3$ | CMe | CH | CH | CH | CH | O | 0 | |
| A-38 | Et | Et | 6-$CF_3$ | CMe | CH | CH | CH | CH | O | 1 | |
| A-39 | Et | Et | 6-$CF_3$ | CMe | CH | CH | CH | CH | O | 2 | |
| A-40 | Et | Et | 6-$CF_3$ | CH | CMe | CH | CH | CH | O | 0 | |
| A-41 | Et | Et | 6-$CF_3$ | CH | CMe | CH | CH | CH | O | 1 | |
| A-42 | Et | Et | 6-$CF_3$ | CH | CMe | CH | CH | CH | O | 2 | |
| A-43 | Et | Et | 6-$CF_3$ | CH | CH | CMe | CH | CH | O | 0 | oil |
| A-44 | Et | Et | 6-$CF_3$ | CH | CH | CMe | CH | CH | O | 1 | |
| A-45 | Et | Et | 6-$CF_3$ | CH | CH | CMe | CH | CH | O | 2 | 111-114 |
| A-46 | Et | Et | 6-$CF_3$ | CH | CH | CF | CH | CH | O | 0 | oil |
| A-47 | Et | Et | 6-$CF_3$ | CH | CH | CF | CH | CH | O | 1 | 109-112 |
| A-48 | Et | Et | 6-$CF_3$ | CH | CH | CF | CH | CH | O | 2 | 115-116 |
| A-49 | Et | Et | 6-$CF_3$ | CH | CH | CCl | CH | CH | O | 0 | oil |
| A-50 | Et | Et | 6-$CF_3$ | CH | CH | CCl | CH | CH | O | 1 | 114-117 |
| A-51 | Et | Et | 6-$CF_3$ | CH | CH | CCl | CH | CH | O | 2 | 162-165 |
| A-52 | Et | Et | 6-$CF_3$ | CH | CH | CBr | CH | CH | O | 0 | oil |
| A-53 | Et | Et | 6-$CF_3$ | CH | CH | CBr | CH | CH | O | 1 | 110-112 |
| A-54 | Et | Et | 6-$CF_3$ | CH | CH | CBr | CH | CH | O | 2 | 121-126 |
| A-55 | Et | Et | 6-$CF_3$ | CH | CH | Cl | CH | CH | O | 0 | oil |
| A-56 | Et | Et | 6-$CF_3$ | CH | CH | Cl | CH | CH | O | 1 | 132-133 |
| A-57 | Et | Et | 6-$CF_3$ | CH | CH | Cl | CH | CH | O | 2 | 133-134 |
| A-58 | Et | Et | 6-$CF_3$ | CH | CH | $CNO_2$ | CH | CH | O | 0 | 96-98 |
| A-59 | Et | Et | 6-$CF_3$ | CH | CH | $CNO_2$ | CH | CH | O | 1 | 152-154 |
| A-60 | Et | Et | 6-$CF_3$ | CH | CH | $CNO_2$ | CH | CH | O | 2 | 142-146 |

TABLE 1-continued

| Compound No. | R¹ | R² | (R⁴)$_m$ | A¹ | A² | A³ | A⁴ | A⁵ | X | n | Melting point |
|---|---|---|---|---|---|---|---|---|---|---|---|
| A-61 | Et | Et | 6-CF₃ | CH | CH | CCN | CH | CH | O | 0 | oil |
| A-62 | Et | Et | 6-CF₃ | CH | CH | CCN | CH | CH | O | 1 | 153-158 |
| A-63 | Et | Et | 6-CF₃ | CH | CH | CCN | CH | CH | O | 2 | oil |
| A-64 | Et | Et | 6-CF₃ | CH | CH | CC₂F₅ | CH | CH | O | 0 | |
| A-65 | Et | Et | 6-CF₃ | CH | CH | CC₂F₅ | CH | CH | O | 1 | |
| A-66 | Et | Et | 6-CF₃ | CH | CH | CC₂F₅ | CH | CH | O | 2 | |
| A-67 | Et | Et | 6-CF₃ | CH | CH | COCF₃ | CH | CH | O | 0 | oil |
| A-68 | Et | Et | 6-CF₃ | CH | CH | COCF₃ | CH | CH | O | 1 | oil |
| A-69 | Et | Et | 6-CF₃ | CH | CH | COCF₃ | CH | CH | O | 2 | oil |
| A-70 | Et | Et | 6-CF₃ | CH | CH | CSCF₃ | CH | CH | O | 0 | oil |
| A-71 | Et | Et | 6-CF₃ | CH | CH | CSCF₃ | CH | CH | O | 1 | oil |
| A-72 | Et | Et | 6-CF₃ | CH | CH | CSCF₃ | CH | CH | O | 2 | oil |
| A-73 | Et | Et | 6-CF₃ | CH | CH | CSOCF₃ | CH | CH | O | 0 | |
| A-74 | Et | Et | 6-CF₃ | CH | CH | CSOCF₃ | CH | CH | O | 1 | |
| A-75 | Et | Et | 6-CF₃ | CH | CH | CSOCF₃ | CH | CH | O | 2 | oil |
| A-79 | Et | Et | 6-CF₃ | CH | CH | CSO₂CF₃ | CH | CH | O | 0 | oil |
| A-80 | Et | Et | 6-CF₃ | CH | CH | CSO₂CF₃ | CH | CH | O | 1 | oil |
| A-81 | Et | Et | 6-CF₃ | CH | CH | CSO₂CF₃ | CH | CH | O | 2 | oil |
| A-82 | Et | Et | 6-CF₃ | CH | CH | CSC₂F₅ | CH | CH | O | 0 | oil |
| A-83 | Et | Et | 6-CF₃ | CH | CH | CSC₂F₅ | CH | CH | O | 1 | oil |
| A-84 | Et | Et | 6-CF₃ | CH | CH | CSC₂F₅ | CH | CH | O | 2 | oil |
| A-85 | Et | Et | 6-CF₃ | CH | CH | CSF₅ | CH | CH | O | 0 | oil |
| A-86 | Et | Et | 6-CF₃ | CH | CH | CSF₅ | CH | CH | O | 1 | 83-86 |
| A-87 | Et | Et | 6-CF₃ | CH | CH | CSF₅ | CH | CH | O | 2 | 116-118 |
| A-88 | Et | Et | 6-CF₃ | CH | CH | CCF(CF₃)₂ | CH | CH | O | 0 | oil |
| A-89 | Et | Et | 6-CF₃ | CH | CH | CCF(CF₃)₂ | CH | CH | O | 1 | oil |
| A-90 | Et | Et | 6-CF₃ | CH | CH | CCF(CF₃)₂ | CH | CH | O | 2 | oil |
| A-91 | Et | Et | 6-CF₃ | CH | CH | CCF₃ | N | CH | O | 0 | 76-77 |
| A-92 | Et | Et | 6-CF₃ | CH | CH | CCF₃ | N | CH | O | 1 | 135-136 |
| A-93 | Et | Et | 6-CF₃ | CH | CH | CCF₃ | N | CH | O | 2 | 143-145 |
| A-94 | Et | Et | 6-CF₃ | CH | CH | CCF₃ | CH | N | O | 0 | |
| A-95 | Et | Et | 6-CF₃ | CH | CH | CCF₃ | CH | N | O | 1 | |
| A-96 | Et | Et | 6-CF₃ | CH | CH | CCF₃ | CH | N | O | 2 | 93-97 |
| A-97 | Et | Me | 6-CF₃ | CH | CH | CCF₃ | CH | CH | S | 0 | |
| A-98 | Et | Me | 6-CF₃ | CH | CH | CCF₃ | CH | CH | S | 1 | |
| A-99 | Et | Me | 6-CF₃ | CH | CH | CCF₃ | CH | CH | S | 2 | 159-161 |
| A-100 | Et | Me | 6-CF₃ | CH | CH | CCF₃ | CH | CH | SO2 | 0 | |
| A-101 | Et | Me | 6-CF₃ | CH | CH | CCF₃ | CH | CH | SO2 | 1 | |
| A-102 | Et | Me | 6-CF₃ | CH | CH | CCF₃ | CH | CH | SO2 | 2 | 247-251 |
| A-103 | Et | Me | 6-CF₃ | CH | CH | COCF₃ | CH | CH | O | 0 | 75-76 |
| A-104 | Et | Me | 6-CF₃ | CH | CH | COCF₃ | CH | CH | O | 1 | 114-116 |
| A-105 | Et | Me | 6-CF₃ | CH | CH | COCF₃ | CH | CH | O | 2 | 132-133 |

The compound of the present invention can be used for prevention and extermination of organisms that are harmful in agriculture or indoors or in the forest, to livestock, or in various situations such as hygiene. Specific usage situations, target harmful organisms, and usage methods will now be shown, but the contents of the present invention are not limited thereto.

The compound of the present invention represented by the formula (1) can also be used for controlling harmful organisms, such as arthropods, mollusks, nematodes, and fungi and bacteria including Eumycota, Myxomycota, Bacteriomycota, and Actinomycota, that damage crops, for example, food crops (e.g., rice, wheat varieties such as barley, wheat, rye, and oats, corn, potato, sweet potato, taro, and beans such as soybeans, adzuki beans, broad beans, peas, common beans, and peanuts), vegetables (e.g., Brassicaceae crops such as cabbage, Chinese cabbage, radish, turnip, broccoli, cauliflower, and Japanese mustard spinach, cucurbitaceous fruits such as pumpkin, cucumber, watermelon, oriental melon, and melon, eggplant, tomato, bell pepper, pepper, okra, spinach, lettuce, lotus root, carrot, burdock, and alliaceous plants such as garlic, onion, and green onion), mushrooms (e.g., shiitake mushroom and mushroom), fruit trees and fruits (e.g., apple, citrus, pear, grape, peach, plum, cherry, walnut, chestnut, almond, banana, and strawberry), seasoning and ornamental crops (e.g., lavender, rosemary, thyme, parsley, pepper, and ginger), industrial crops (e.g., tobacco, tea, sugar beet, sugar cane, hops, cotton, hemp, olive, rubber, and coffee), pasture and forage crops (e.g., timothy, clover, alfalfa, corn, sorghums, orchard grass, gramineous grass, and leguminous grass), lawn grass (e.g., manila grass and bent grass), forest trees (e.g., Sakhalin fir, Todo fir, pine trees, cypress, cedar, and Japanese cypress), and ornamental plants (e.g., herbs and flowers such as chrysanthemum, rose, carnation, and orchid and garden trees such as ginkgo, cherry blossoms, and Japanese laurel). Specific examples of the harmful organisms include the followings.

Adults, larvae, and eggs of pests belonging to Lepidoptera of Arthropoda Insecta, for example, Noctuidae, such as *Helicoverpa armigera*, *Heliothis* spp., *Agrotis segetum*, *Autographa nigrisigna*, *Trichoplusia ni*, *Mamestra brassicae*, *Spodoptera exigua*, and *Spodoptera litura*; Yponomeutidae, such as *Plutella xylostella*; Tortricidae, such as *Adoxophyes orana fasciata*, *Adoxophyes honmai*, *Archips fuscocupreanus*, *Homona magnanima*, *Caloptilia theivora*, and *Grapholita molesta*; Psychidae, such as *Eumeta minuscula*; Lyonetiidae, such as *Lyonetia prunifoliella malinella* and *Lyonetia clerkella*; Phyllocnistinae, such as *Phyllocnistis citrella*; Gracillariidae, such as *Phyllonorycter ringoniella*;

Acrolepiidae, such as *Acrolepiopsis sapporensis*; Sesiidae, such as *Synanthedin hector*; Stathmopodidae, such as

*Stathmopoda masinissa*; Gelechiidae, such as *Pectinophora gossypiella*; Carposinidae, such as *Carposina niponensis*; Cossidae, such as *Cossus jezoensis*; Tineidae, such as *Nemapogon granella*; Limacodidae, such as *Monema flavecens, Parasa lepida*, and *Scopelodes contracus*; Crambidae, such as *Chilo suppressalis, Scirpophaga incertulas, Cnaphalocrocis medinalis, Hellulla undalis, Conogethes punctiferlis, Diaphania indica*, and *Parapediasia teterrella*; Pyralidae, such as *Locastra muscosalis*; Hesperiidae, such as *Parnara guttata*; Papilionidae, such as *Papilio Xuthus*; Pieridae, such as *Pieris rapae crucivora*; Lycaenidae, such as *Lampides boeticus*; Geometridae, such as *Ascotis selenaria*; Sphingidae, such as *Agrius convolvuli*; Notodontidae, such as *Phalera flavescens*; Lasiocampidae, such as *Malacosoma neustrium testaceum*; Saturniidae, such as *Saturnia japonica*; Lymantriidae, such as *Euproctis pseudoconspersa, Orgyia thyellina*, and *Telochurus recens approximans*; Arctiidae, such as *Spilosoma imparilis* and *Hyphantria cunea*; and *Endopiza viteana* and *Laspeyresia pomonella*, Adults, larvae, and eggs of pests belonging to Coleoptera, for example, Scarabaeidae, such as *Anomala cuprea, Popillia japonica, Oxycetonia jucunda*, and *Anomala geniculate*; Buprestidae, such as *Agrilus auriventris*; Elaterinae, such as *Melanotus fortnumi*; Coccinellidae, such as *Epilachna vigintioctopunctata*; Cerambycidae, such as *Anoplophora malasiaca* and *Xylotrechus pyrrhoderus*; Chrysomelidae, such as *Aulacophora femoralis, Diabrotica* spp., *Phyllotreta striolata, Cassida nebulosa, Phaedon brassicae, Oulema oryzae, Epilachna varivestis*, and *Leptinotarsa decemlineata*; Attelabidae, such as *Rhynchites heros*; Brentidae, such as *Cylas formicarius*; Curculionidae, such as *Curculio sikkimensis, Lissorhoptrus oryzophilus, Anthonomus gradis grandis*, and *Sphenophrus venatus vestitus*; and Nitidulidae, such as *Epuraea domina*, Adults, larvae, and eggs of pests belonging to Heteroptera of Hemiptera, for example, Pentatomidae, such as *Eurydema rugosum, Eysarcoris lewisi, Eysarcoris parvus, Nezara viridula, Plautia stali*, and *Halymorpha mista*; Urostylididae, such as *Urochela luteovoria*; Lygaeidae, such as *Togo hemipterus*; Coreidae, such as *Riptortus clavatus* and *Cletus punctiger*; Alydidae, such as *Leptocorisa chinensis*; Pyrrhocoridae, such as *Dysdeercus cingulatus*; Tingidae, such as *Stephanitis nashi* and *Stephanitis pyrioides*; Miridae, such as *Apolygus spinolai, Stenotus rubrovittalus*, and *Trigonotylus coelestialium*; and Plataspidae, such as *Megacopta punctatissimum*, Adults, larvae, and eggs of pests belonging to Homoptera of Hemiptera, for example, Cicadiae, such as *Platypleura kaempferi*; Cicadellidae, such as *Arboridia apicalis, Empoasca onukii, Nephotettix cincticeps*, and *Nephotettix virescens*; Dilphacidae, such as *Laodelphax striatellus, Nilaparvata lugens*, and *Sogatella furcifera*; Flatidae, such as *Geisha distinctissima*; Psyllidae, *Psylla pyrisuga* and *Diaphorina citri*; Aleyrodidae, such as *Aleurocanthus spiniferus, Bemisia argentifolii*, various biotypes of *Bemisia tabaci, Dialeurodes citri*, and *Trialeurodes vaporariorum*; Phylloxeridae, such as *Viteus vitifolii*; Aphididae, such as *Aphis citricola, Aphis craccivora, Aphis gossypii, Aulacorthum solani, Brevicoryne brassicae, Toxoptera aurantii, Toxoptera citricidus, Aulacorthum magnoliae, Schizaphis piricola, Nippolachnus piri, Lipaphis erysimi, Hyalopterus pruni, Pleotrichophorus chrysanthemi, Macrosiphoniella sanborni, Megoura crassicauda, Sitobion ibarae, Macrosiphum euphorbiae, Myzus varians, Myzus persicae, Rhopalosiphum rufiabdominalis, Rhopalosiphum padi, Sitobion akebiae*, and *Eriosoma lanigerum*; Monophlebidae, such as *Icerya* purchase; Pseudococcidae, such as *Pseudococcus comstocki, Phenacoccus viburnae*, and *Phenacoccus kraunhiae*; Coccidae, such as *Ceroplastes ceriferus* and *Ceroplastes rubens*; and Diaspididae, such as *Aonidiella aurantii, Comstockaspis perniciosa, Pseudaulacaspis pentagoa*, and *Unaspis yanonensis*, Adults, larvae, and eggs of pests belonging to Thysanoptera, for example, Thripidae, such as *Scirtothrips dorsalis, Thrips palmi, Thrips tabaci, Thrips setosus, Frankliniella intonsa, Frankliniella occidentalis*, and *Heliothrips haemorrhoidalis*; and Phlaeothripidae, such as *Ponticulothrips diospyrosi* and *Haplothrips aculeatus*, Adults, larvae, and eggs of pests belonging to Hymenoptera, for example, Tenthredinidae, such as *Athalia rosae ruficornis* and *Arge pagana*; Argidae, such as *Arge mali*; Cynipidae, such as *Dryocsmus kuriphilus*; Megachilidae, such as *Megachile nipponica nipponica*; and Formicidae, such as *Formica japonica, Camponotus kiusiuensis, Lasius fuliginosus*, and *Solenopsis richteri* (*S. invicta, S. geminate*), Adults, larvae, and eggs of pests belonging to Diptera, for example, Cecidomyiidae, such as *Asphondylia yushimai*; Tephritidae, such as *Rhacochlaena japonica* and *Bactrocera cucurbitae*; Ephydridae, such as *Hydrellia griseola*; Drosophilidae, such as *Drosophila suzukii*; Agromyzidae, such as *Liriomyza trifolii, Liriomyza sativae, Chromatomyia horticola, Agromyza oryzae*, and *Liriomyza bryoniae*; and Anthomyiidae, such as *Delia platura* and *Delia antiqua*, Adults, larvae, and eggs of pests belonging to Orthoptera, for example, Acrididae, such as *Locusta migratoria*; Tettigoniidae, such as *Ruspolia lineosa*; Gryllidae, such as *Teleogryllus emma* and *Truljalia hibinonis*; Gryllotalpidae, such as *Gryllotalpa orientalis*; and Acrididae, such as *Oxya yezoensis*, Adults, larvae, and eggs of pests belonging to Isoptera, for example, Termitidae, such as *Odontotermes formosanus*, Adults, larvae, and eggs of pests belonging to *Dermaptera*, for example, Labiduridae, such as *Labidura riparia*, Adults, larvae, and eggs of pests belonging to Collembola of Arthropoda Parainsecta, for example, Sminthuridae, such as *Sminthurus viridis*; Onychiuridae, such as *Onychiurus matsumotoi*; adults, larvae, and eggs of pests belonging to Isopada of Arthropoda Malacostraca, for example, Armadillidae, such as *Armadillidium vulgare*, Adults, larvae, and eggs of pests belonging to Acari of Arthropoda Arachinida, for example, Tarsonemidae, such as *Polyphagotarsonemus latus* and *Phytonemus pallidus*; Eupodidae, such as *Penthaleus major*; Tenuipalpidae, such as *Brevipalpus lewisi* and *Brevipalpus phoenicis*; Tetranychidae, such as *Panonychus citri, Panonychus ulmi, Tetranychus urticae, Tetranychus kanzawai, Amphitetranychus viennensis, Oligonychus ununguis, Bryobia eharai, Eotetranychus kankitus*, and *Bryobia praetiosa*; Eriophyidae, such as *Aculus Schlechtendali, Aculops pelekassi, Phyllocoptruta citri, Eriophyes chibaensis, Aceria tulipae, Colomerus vitis, Aculus fockeui*, and *Calacarus carinatus*; and Acaridae, such as *Tyrophagus putrescentiae* and *Rhizoglyphus robini*, and Pests belonging to Architaenioglossa of Mollusca Gastropoda, for example, Pilidae, such as *Pomacea caniculate*, pests belonging to Plumonata, for example, Achatinidae, such as *Achatina fulica*; Philomycidae, such as *Meghimatium bilineatum*; Milacidae, such as *Milax gagates*; Limacidae, such as *Lehmannina valentiana*; and Bradybaenidae, such as *Acusta despecta sieboldiana*, Pests belonging to Tylenchida of Nematoda Secernentea, for example, Anguinidae, such as *Ditylenchus destructor*; Belonolaimidae, such as *Tylenchorhynchus claytoni*; Pratylenchidae, such as *Pratylenchus penetrans* and *Pratylenchus coffeae*;

Hoplolaimidae, such as *Helicotylenchus dihystera*; Heteroderidae, such as *Globodera rostochiensis*; Meloidogynidae, such as *Meloidogyne incognita*; Criconematidae, such as *Criconema jaejuense*; Anguinidae, such as *Nothotylenchus acris*; Aphelenchoididae, such as *Aphelecchoides fragarriae*, pests belonging to Dorylaimida of Adenophorea, for example, Longidoridae, such as *Xiphinema* sp.; and Trichodoridae, such as *Trichodorus* sp., and Pests belonging to fungi or bacteria, such as Eumycota, Myxomycota, Bacteriomycota, and Actinomycota.

Examples of the disease to which the compound of the present invention represented by the formula (1) can be applied include rice diseases, such as blast disease (*Pyricularia oryzae*), brown spot (*Cochliobolus miyabeanus*), sheath blight (*Rhizoctonia solani*), bacterial palea browning (*Pantoea ananatis*), brown stripe disease (*Acidovorax avene* subsp. *avenae*), sheath brown rot (*Pseudomonas fuscovaginae*), bacterial leaf blight (*Xanthomonas oryzae* pv. *oryzae*), and bacterial seedling blight (*Burkholderia plantarii*); wheat diseases, such as powdery mildew (*Erysiphe graminis*), red mildew (*Gibberella zeae*), leaf rust (*Puccinia striiformis, P. graminis, P. recondita*, and *P. hordei*), snow mold (*Typhula* sp. and *Micronectriella nivalis*), loose kernel smut (*Ustilago tritici* and *U. nuda*), stinking smut (*Tilletia caries*), eye spot (*Pseudocercosporella herpotrichoides*), leaf blotch (*Rhynchosporium secalis*), leaf blight (*Septoria tritici*), glume blotch (*Leptosphaeria nodorum*), net blotch (*Pyrenophora teres*), zonate leaf spot (*Helminthosporium zonatum* Ikata), and bacterial stripe blight (*Pseudomonas syringae* pv. *japonica*); citrus fruit diseases, such as black spot (*Diaporthe citri*), spot anthracnose (*Elsinoe fawcetti*), fruit rot (*Penicillium digitatum* and *P. italicum*), brown rot (*Phytophthora citrophthora* and *P. nicotianae*), and scab (*Phyllosticta citricarpa*); apple diseases, such as Molinia leaf blight (*Monilinia mali*), valsa canker (*Valsa mali*), powdery mildew (*Podosphaera leucotricha*), alternaria leaf spot (*Alternaria mali*), scab (*Venturia inaequalis*), black spot (*Mycospherella pomi*), bitter rot (*Colletotrichum acutatum*), ring rot (*Botryosphaeria berengeriana*), rust (*Gymnosporangium yamadae*), and brown rot (*Monilinia fructicola*);

Pear diseases, such as scab (*Venturia nashicola* and *V. pirina*), purple spot (*Alternaria kikuchiana*), rust (*Gymnosporangium haraeanum*), and brown rot (*Monilinia fructigena*); peach diseases, such as brown rot (*Monilinia fructicola*), scab (*Cladosporium carpophilum*), Phomopsis rot (*Phomopsis* sp.), and bacterial shot hole (*Brenneria nigrifluens*); grape diseases, such as anthracnose (*Elsinoe ampelina*), ripe rot (*Colletotrichum acutatum*), powdery mildew (*Uncinula necator*), rust (*Phakopsora ampelopsidis*), black rot (*Guignardia bidwellii*), downy mildew (*Plasmopara viticola*), brown rot (*Monilinia fructigena*), scab (*Cladosporium viticolum*), gray mold (*Botrytis cinerea*), and crown gall (*Agrobacterium vitis*); persimmon diseases, such as bitter rot (*Gloeosporium kaki*), and angular leaf spot (*Cercospora kaki* and *Mycoshaerella nawae*); gourd diseases, such as bitter rot (*Colletotrichum lagenarium*), powdery mildew (*Sphaerotheca fuliginea* and *Oidiopsis taurica*), gummy stem blight (*Didymella bryoniae*), fusarium wilt (*Fusarium oxysporum*), downy mildew (*Pseudoperonospora cubensis*), phytophthora rot (*Phytophthora* sp.), and damping-off (*Pythium* sp.); cucumber diseases, such as bacterial spot (*Pseudomonas syringae* pv. *lochrymans*), marginal blight (*Pseudomonas viridiflava*), and bacterial brown spot (*Xanthomonas campestris* pv. *cucurbitae*); melon diseases, such as bacterial brown spot (*Xanthomonas campestris* pv. cucurbitae), hairy rot (*Agrobacterium rhizogens*), and root tumor (*Streptomyces* sp.); watermelon diseases, such as bacterial fruit blotch (*Acidovorax avenae* pv. *citrulli*); Solanaceae vegetable diseases, such as bacterial wilt (*Ralstonia solanacearum*); tomato diseases, such as ring rot (*Alternaria solani*), leaf mold (*Cladosporium fulvum*), phytophthora rot (*Phytophthora infestans*), bacterial canker (*Clavibacter michiganense* subsp. *michiganense*), stem necrosis (*Pseudomonas corrugata*), and bacterial soft rot (*Pectobacterium carotovorum* subsp. *carotovorum*); eggplant diseases, such as brown spot (*Phomopsis vexans*) and powdery mildew (*Erysiphe cichoracearum*); Brassicaceae vegetable diseases, such as purple spot (*Alternaria japonica*), white spot (*Cercosporella brassicae*), and soft rot (*Pectobacterium carotovorum* subsp. *carotovorum*);

Cabbage diseases, such as soft rot (*Pseudomonas syringae* pv. *marginalis*) and black rot (*Xanthomonas campestris* pv. *campestris*); lettuce diseases, such as soft rot (*Pseudomonas cichorii* and *Pseudomonas viridiflava*) and bacterial spot (*Xanthomonas campestris* pv. *vitians*); green onion diseases, such as rust (*Puccinia allii*); soybean diseases, such as purple seed strain (*Cercospora kikuchii*), Sphaoeloma scab (*Elsinoe glycines*), and black spot (*Diaporthe phaseolorum* var. *sojae*); kidney bean diseases, such as bitter rot (*Colletotrichum lindemthianum*); peanut diseases, such as leaf spot (*Cercospora personata*) and brown leaf spot (*Cercospora arachidicola*); pea diseases, such as powdery mildew (*Erysiphe pisi*); potato diseases, such as early blight (*Alternaria solani*), phytophthora rot (*Phytophthora infestans*), and rhizoctonia rot (*Rhizoctonia solani*); strawberry diseases, such as powdery mildew (*Sphaerotheca humuli*); tea diseases, such as net blister blight (*Exobasidium reticulatum*), leaf spot (*Elsinoe leucospila*), bacterial shoot blight (*Pseudomonas syringae* pv. *theae*), and bacterial canker (*Xanthomonas campestris* pv. *theicola*); tobacco diseases, such as rust (*Alternaria longipes*), powdery mildew (*Erysiphe cichoracearum*), bitter rot (*Colletotrichum tabacum*), downy mildew (*Peronospora tabacina*), phytophthora rot (*Phytophthora nicotianae*), bacterial wilt (*Ralstonia solanacearum*), and hollow stalk (*Pectobacterium carotovorum* subsp. *carotovorum*); sugar beet diseases, such as brown leaf spot (*Cercospora beticola*) and damping-off (*Aphanomyces cochliodes*); rose diseases, such as scab (*Diplocarpon rosae*) and powdery mildew (*Sphaerotheca pannosa*); chrysanthemum diseases, such as brown leaf spot (*Septoria chrysanthemi-indici*), rust (*Puccinia horiana*), and crown gall (*Agrobacterium tumefaciens*); diseases of various crops, for example, eggplant, cucumber, and lettuce, such as gray mold (*Botrytis cinerea*) and sclerotinia rot (*Sclerotinia sclerotiorum*); lawn diseases, such as snow mold (*Pythium iwayamai, Tyohula incarnate, Fusarium nivale*, and *Sclerotinia borealis*), powdery mildew (*Erysiphe graminis*), fairy ring disease (*Lycoperdon perlatum, Lepista subnudo*, and *Marasmius oreades*), para-rhizoctonia rot (*Ceratobasidium* spp.), bacterial wilt (*Gaemannomyces graminis*), Curvularia leaf blight (*Curvularia geniculata*), rhizoctonia rot (*Rhizoctonia solani*), pythium root rot (*Pythium periplocum* and *Pythium vanterpoolii*), rust (*Puccinia* spp.), and dollar spot disease (*Sclerotinia homoeocarpa*).; and bent grass diseases, such as bacterial shoot blight (*Pythium aphanidermatum*) and bitter rot (*Colletotrichum* sp.).

The compound of the present invention represented by the formula (1) can also be used for controlling arthropods and fungi that are active indoors in buildings, including ordinary houses, that perpetrate or rot wood and its processed wooden furniture, stored food, clothes, books, etc., and that damage our lives. Specific examples of the harmful organisms include the followings.

Adults, larvae, and eggs of pests belonging to Isoptera of Arthropoda Insecta, for example, Phinotermitidae, such as *Coptotermes formosanus, Reticulitermes speratus*, other termites of *Reticulitermes* spp. (e.g., *Reticulitermes hesperus, R. tibialis, R. flavipes, R. lucifugus*, and *R. santonensis*), and *Incisitermes minor*; Termitidae, such as *Odontotermes formosanus*; Termopsidae, such as *Hodotermopsis japonica*; and Kalotermitidae, such as *Cryptotermes domesticus*, Adults, larvae, and eggs of pests belonging to Coleoptera, for example, Rhynchophoridae, such as *Sitophilus zeamais* and *Sitophilus zeamais*; Bruchidae, such as *Callosobruchus chinensis, Bruchus pisorum*, and *Bruchus rufimanus*; Tenebrionidae, such as *Tribolium castaneum* and *Tribolium confusum*; Silvanidae, such as *Oryzaephilus surinamensis* and *Cryptolestes pusillus*; Anobiidae, such as *Lasioderma serricorne* and *Stegobium paniceum*; Dermesridae, such as *Attagenus unicolor japonicus, Anthrenus verbasci*, and *Dermestes maculatus*; Ptinidae, such as *Gibbium aequinnoctiale*; Bostrychidae, such as *Dinoderus minutus* and *Rhizopertha dominica*; and Lyctidae, such as *Lyctus brunneus*, Adults, larvae, and eggs of pests belonging to Lepidoptera, for example, Pyralidae, such as *Cadra cautella, Ephestia kuehniella*, and *Plodia interpunctella*; Gelechiidae, such as *Sitotroga cerealella*; Tineidae, such as *Tinea translucens* and *Tineola bisselliella*, adults, larvae, and eggs of pests belonging to Psocoptera, for example, Trogiidae, such as *Lepinotus reticulatus*; and Liposcelidae, such as *Liposcelis bostrychophilus*, Adults, larvae, and eggs of pests belonging to Blattodea, for example, Blattellidae, such as *Blattella germanica*; and Blattidae, such as *Periplaneta fuliginosa* and *Periplaneta japonica*, adults, larvae, and eggs of pests belonging to Hymenoptera, for example, Formicidae, such as *Monomorium pharaonic* and *Monomorium nipponense*, Adults, larvae, and eggs of pests belonging to Zygentoma, for example, Lepismatidae, such as *Ctenolepisma villosa* and *Lepisma saccharina*, Adults, larvae, and eggs of pests belonging to Diptera, for example, Drosophilidae, such as *Drosophila melangogaster*; and Piophilidae, such as *Piophila casei*, Adults, larvae, and eggs of pests belonging to Acari of Arthropoda Arachnida, for example, Acaridae, such as *Tyrophagus putrescentiae* and *Lardoglyphus konoi*; and Carpoglyphidae, such as *Carpoglyphus lactis*, and Wood-rotting fungi, such as *Tyromyces palustris* and *Coriolus versicolor*; and Material deterioration microorganisms, such as *Aspergillus niger, Aspergillus terreus, Aureobasidium pullulans, Chaetomium globosum, Cladosporium cladosporioides, Eurotium tonophilus, Fusarium moniliforme, Gliocladium virens, Myrothecium verrucaria, Penicillium citrinum, Penicillium funiculosum*, and *Rhizopus oryzae*.

The compound of the present invention represented by the formula (1) can also be used for controlling harmful organisms that are injurious to trees in natural forests, planted forests, and urban green spaces or that weaken the trees. Specific examples of the harmful organisms include the followings.

Adults, larvae, and eggs of pests belonging to Lepidoptera of Arthropoda Insecta, for example, Lymantriidae, such as *Calliteara argentata, Euproctis pseudoconspersa, Orygia recens approximans, Euproctis subflava*, and *Lymantria dispar*; Lasiocampidae, such as *Malacosoma neustria testacea, Dendrolimus spectabilis*, and *Dendrolimus superans*; Pyralidae, such as *Crytoblabes loxiella*; Noctuidae, such as *Agrotis segetum*; Tortricidae, such as *Ptycholoma lecheana circumclusana, Cydia kurokoi*, and *Cydia cryptomeriae*; Arctiidae, such as *Spilosoma imparilis* and *Hyphantria cunea*; Nepticulidae, such as *Stigmella castanopsiella*; Limacodidae, such as *Parasa lepida, Scopelodes contracus*, and *Microleon longipalpis*, adults, larvae, and eggs of pests belonging to Coleoptera, for example, Scarabaeidae, such as *Anomala rufocuprea* and *Heptophylla picea*; Buprestidae, such as *Agrilus spinipennis*; Cerambycidae, such as *Monochamus alternatus*; Chrysomelidae, such as *Basilepta pallidula*; Curculionidae, such as *Scepticus griseus* and *Shirahoshizo insidiosus*; Rhynchophoridae, such as *Sipalinus gigas*; Scolytidae, such as *Tomicus piniperda* and *Indocryphalus aceris*; and Bostrychidae, such as *Rhizopertha dominica*, Adults, larvae, and eggs of pests belonging to Hemiptera, for example, Aphididae, such as *Cinara todocola*; Adelgidae, such as *Adelges japonicus*; Diaspididae, such as *Aspidiotus cryptomeriae*; and Coccidae, such as *Ceroplastes ceriferus*, Adults, larvae, and eggs of pests belonging to Hymenoptera, for example, Tenthredinidae, such as *Pachynematus itoi*; Diprionidae, such as *Neodiprion sertifer*; and Cynipidae, such as *Dryocosmus kuriohilus*, adults, larvae, and eggs of pests belonging to Diptera, for example, Tipulidae, such as *Tipula aino*; Anthomyiidae, such as *Strobilomyia laricicola*; and Cecidomyiidae, such as *Contarinia inouyei* and *Contarinia matsusintome*, Adults, larvae, and eggs of pests belonging to Acari of Arthropoda Arachnida, for example, *Oligonichus hondoensis* and *Oligonichus ununguis*, and Pests belonging to Tylenchida of Nematoda Secernentea, for example, Parasitaphelenchidae, such as *Bursaphelenchus xylophilus*.

The compound of the present invention represented by the formula (1) can also be used for preventing, treating, or controlling arthropods, nematodes, trematodes, cestodes, and protozoans that internally or externally parasitize livestock and pets, i.e., vertebrates, especially warm-blooded vertebrates, such as cows, sheep, goats, horses, pigs, fowls, dogs, cats, and fish. Examples of the target animal species include, in addition to the above, pets and experimental animals, e.g., rodents, such as mice, rats, hamsters, and squirrels; carnivorous animals, such as ferrets; and birds, such as ducks and pigeons. Specific examples of the harmful organisms include the followings.

Adults, larvae, and eggs of pests belonging to Diptera of Arthropoda Insecta, for example, Tabanidae, such as *Tabanus rufidens* and *Tabanus chrysurus*; Muscidae, such as *Musca bezzii, Musca domestica*, and *Stomoxys calcitrans*; Gasterophilidae, such as *Gasterophilus intestinalis*; Hypodermatidaed, such as *Hypoderma bovis*; Oestridae, such as *Oestrus ovis*; Calliphoridae, such as *Aldrichina graham*; Phoridae, such as *Megaselia spiracularis*; Sepsidae, such as *Sepsis punctum*; Psychodidae, such as *Telmatoscopus albipunctatus* and *Psychoda alternata*; Culicidae, such as *Culex pipiens molestus, Culex pipiens pallens, Anopheles sinensis, Culex pipiens triaeniorhynchus summorosus*, and *Ades albopictus*; Simuliidae, such as *Simulium iwatense* and *Prosimulium yezoense*; and Ceratopogonidae, such as *Culicoides schulzei* and *Culicoides arakawae*, Adults, larvae, and eggs of pests belonging to Siphonaptera, for example, Pulicidae, such as *Pulex irritans* and *Ctenocephalides canis*, Adults, larvae, and eggs of pests belonging to *Anoplura*, for example, Echinophthiriidae, such as Haematopinidae suis and Haematopinidae *eurysternus*; Trichodectidae, such as *Damalinia bovis*; Linognathidae, such as *Linognathus vituli*; and Menoponidae, such as *Menopon gallinae*, Adults, larvae, and eggs of pests belonging to Acari of Arthropoda Arachnida, for example, Varroidae, such as *Varroa jacobsoni*; Ixodidae, such as *Haemaphysalis longicornis, Ixodes ovatus, Boophilus microplus*, and *Amblyomma testudinarium*; Macronyssidae, such as *Ornithonyssus sylvialum*; Dermanyssidae, such as *Dermanyssus gallinae*; Demodicidae, such as *Demodex phylloides*; Sarcoptidae, such as *Sarcoptes scabiei bovis* and *Knemidocoptes mutans*; and Psoroptidae, such as *Otodectes cynotis* and *Psoroptes communis*, and Pests belonging to Strongylida of Nematoda Secernentea, for example, *Bunostomum phlebotomum, Stephanurus dentatus, Metastrongylus elongatus, Trichostrongylus orientalis*, and *Oesophagostomum radiatum;*

Ascaridida, for example, *Ascaris suum* and *Ascaridia galli*; Platyhelminthes Trematoda, for example, *Schistosoma japonicum, Fasciola hepatica* Linnaeus, *Paramphistonum cervi, Paragonimum westermanii*, and *Prosthogonimus ovatus*; and Cestoda, for example, *Anoplocephala perfoliata, Moniezia expansa, Moniezia benedeni, Raillietina tetragona, Raillietina echinobothrida*, and *Raillietina cesticillus*, Pests belonging to Rhizomastigida of Phylum Protozoa Flagellat, for example, *Histomonas*; Protomastigida, for example, *Leishmania* and *Trypanosoma*; Hypermastigida, for example, Giardia; and Trichomonadida, for example, *Trichomonas*, Amoebida of Sarcodina, for example, *Entamoeba*, and Piroplasmia of Sporozoea, for example, Theilaria and *Babesia*; and Telosporea, for example, *Eimeria, Plasmodium*, and *Toxoplasma*.

The compound of the present invention represented by the formula (1) can also be used for exterminating harmful organisms that cause direct harm or discomfort to the human body or for maintaining public health against harmful organisms that carry and transmit pathogens. Specific examples of the harmful organisms include the followings.

Adults, larvae, and eggs of pests belonging to Lepidoptera of Arthropoda Insecta, for example, Lymantriidae, such as *Sphrageidus similis*; Lasiocampidae, such as *Kunugia undans*; Limacodidae, such as *Parasa consocia*; and Zygaenidae, such as *Artona martini*, Adults, larvae, and eggs of pests belonging to Coleoptera, for example, Oedemeridae, such as *Xanthochroa waterhousei*; Meloidae, such as *Epicauta gorhani*; and Staphylinidae, such as *Paederus fuscipes*, Adults, larvae, and eggs of pests belonging to Hymenoptera, for example, Vespidae, such as *Vespa simillima xanthoptera*; Formicidae, such as *Brachyponera chinensis*; and Pompilidae, such as *Batozonellus annulatus*, Adults, larvae, and eggs of pests belonging to Diptera, for example, Culicidae, such as *Armigeres subalbatus*; Ceratopogonidae, such as *Culicoides nipponensis*; Chironomidae, such as *Chironomus yoshimatsui*; Simuliidae, such as *Simulium nikkoense*; Tabanidae, such as *Hirosia humilis*; Muscidae, such as *Musca domestica*; Fanniidae, such as *Fannia canicularis*; Calliphoridae, such as *Phormia regina*; and Calliphoridae, such as *Sarcophaga peregrina*, Adults, larvae, and eggs of pests belonging to Siphonaptera, for example, Pulicidae, such as *Pulex irritans*, Adults, larvae, and eggs of pests belonging to Blattodea, for example, Blattellidae, such as *Blattella germanica*; and Blattidae, such as *Periplaneta americana, Periplaneta fuliginosa*, and *Periplaneta japonica*, Adults, larvae, and eggs of pests belonging to Orthoptera, for example, Gryllacrididae, such as *Diestrammena japonica* and *Diestrammena apicalis*, Adults, larvae, and eggs of pests belonging to *Anoplura*, for example, Pediculidae, such as *Pediculus humanus humanus*); and Pthiridae, such as *Phthirius pubis*, Adults, larvae, and eggs of pests belonging to Hemiptera, for example, Cimicidae, such as *Cimex lectularius*; and Reduviidae, such as *Isyndus obscurus*, Adults, larvae, and eggs of pests belonging to Collembola of Arthropoda Parainsecta, for example, Hypogastruidae, such as *Hypogastrura communis*, Adults, larvae, and eggs of pests belonging to Acari of Arthropoda Arachnida, for example, Ixodidae, such as *Ixodes persulcatus*; Macronyssidae, such as *Ornithonyssus bacoti*; Cheyletidae, such as *Chelacaropsis moorei*; Pyemotidae, such as *Pyemotes ventricosus*; Demodicidae, such as *Demodex folliculorum*; Pyroglyphidae, such as *Dermotophagoides pteronyssinus*; Sarcoptidae, such as *Sarcoptes scabiei*; and Trombiculidae, such as *Trombicula akamushi*, Adults, larvae, and eggs of pests belonging to Araneae, for example, Clubionidae, such as *Chiracanthium japonicum*; Sparassidae, such as *Heteropoda venatoria*; Pholcidae, such as *Spermophora senoculata* and *Pholcus phalangioides*; Urocteridae, such as *Uroctea compactilis*; and Salticidae, such as *Plexippus paykulli* and *Plexippus adansoni*, Adults, larvae, and eggs of pests belonging to Scorpiones, for example, Buthidae, such as *Isometrus europaeus*, Adults, larvae, and eggs of pests belonging to Scolopendromorpha of Arthropoda Chilopoda, for example, Scolopendridae, such as *Scolopendra subspinipes mutilans* and *Scolopendra subspinipes japonica*, Adults, larvae, and eggs of pests belonging to Scutigeromorpha, for example, Scutigeridae, such as *Thereuronema hilgendofi*, Adults, larvae, and eggs of pests belonging to Polydesmida of Arthropoda Diplopoda, for example, Paradoxosomatidae, such as *Oxidus gracilis*, Adults, larvae, and eggs of pests belonging to Isopoda of Arthropoda Crustacea, for example, Porcellionidae, such as *Porcellio scaber*, and Pests belonging to Gnathobdellida of Annelida Hirudinea, for example, Haemadipsidae, such as *Haemadipsa zeylanica japonica*, and Eumycetes, for example, *Trichophyton* fungi, such as *Trichophyton rubrum* and *Trichophyton mentagrophytes; Candida* fungi, such as *Candida albicans*; and *Aspergillus* fungi, such as *Aspergillus fumigatus*, gram negative bacteria, for example, *Escherichia coli* and *Pseudomonas aeruginosa*, and gram positive bacteria, for example, *Staphylococcus aureus*.

The compound of the present invention represented by the formula (1) is particularly valuable, in controlling harmful organisms that damage crops, trees in natural forests, planted forests, and urban green spaces, and ornamental plants, such as arthropods, gastropods, nematodes, and fungi. In such a situation, the compound of the present invention can also be present in a commercially useful formulation and a use form prepared from such a formulation as a mixed agent with another active compound such as an insecticide, a miticide, a nematicide, a fungicide, a synergist, a plant growth regulator, a poison bait, or an herbicide.

The use form can be, for example, a water dispersible powder, a granular water dispersible powder, a dry flowable agent, a water-soluble agent, an emulsion agent, a liquid agent, an oil agent, a flowable agent such as a suspension agent in water or an emulsion agent in water, capsules, a powder formulation, granules, fine granules, a bait, tablets, a spray formulation, a haze formulation, or an aerosol formulation. In order to form these formulations, various pesticidal adjuvants that have been conventionally used in the technical field of agricultural and horticultural chemical agent can be appropriately used. These pesticidal adjuvants can be used for the purpose of, for example, improvement of the effect, stabilization, and improvement of the dispersibility of agricultural and horticultural chemical agents.

Examples of the pesticidal adjuvant include a carrier (diluent), a spreading agent, an emulsifier, a wetting agent, a dispersant, and a disintegrant. Examples of the liquid carrier include water; aromatic hydrocarbons, such as toluene and xylene; alcohols, such as methanol, butanol, and glycol; ketones, such as acetone; amides, such as dimethylformamide; sulfoxides, such as dimethyl sulfoxide; and methylnaphthalene, cyclohexane, animal and vegetable oils, and fatty acid. Examples of the solid carrier include clay, kaolin, talc, diatomaceous earth, silica, calcium carbonate, montmorillonite, bentonite, feldspar, quartz, alumina, sawdust, nitrocellulose, starch, and gum Arabic.

As the emulsifier or the dispersant, ordinary surfactants can be used. For example, an anionic surfactant, a cationic surfactant, a nonionic surfactant, or an amphoteric surfactant, such as higher alcohol sodium sulfate, stearyl trimethyl ammonium chloride, polyoxyethylene alkylphenyl ether, and lauryl betaine, can be used.

In addition, for example, a spreading agent; a wetting agent, such as dialkyl sulfosuccinate; a sticking agent, such as carboxymethyl cellulose or polyvinyl alcohol; and a disintegrant, such as sodium lignin sulfonate or sodium lauryl sulfate can be used.

One of the compounds of the present invention may be used alone as an active ingredient, or a combination of two or more thereof may be used as an active ingredient. In these formulations, the content of the compound of the present invention as the active ingredient is, for example, 0.01 to 99.5 mass % and is preferably selected from a range of 0.5 to 90 mass % and may be appropriately determined according to various conditions such as formulation form and application method. For example, it is possible to manufacture a powder formulation so as to contain about 0.5 to 20 mass %, preferably 1 to 10 mass %, of the active ingredient, a water dispersible powder so as to contain about 1 to 90 mass %, preferably 10 to 80 mass %, of the active ingredient, and an emulsion agent so as to contain about 1 to 90 mass %, preferably 10 to 40 mass %, of the active ingredient.

In order to control arthropods, gastropods, nematodes, or fungi, usually, the formulation can be used by spraying to leaves and stems of plants in a place where the damage caused by these harmful organisms is occurring or can occur or by being allowed to be absorbed from roots by treating soil or the like through, for example, soil all layer mixing, plating row application, bed soil mixing, cell seedling, planting hole treatment, plant root treatment, top dressing, rice plant box treatment, or submerged application. In addition, the formulation can be used by seed treatment, such as soaking of seeds in chemicals, seed powder coating, or calper treatment, application to nourishing solution in nutriculture (hydroponic culture), or smoking or trunk injection. In the use, while it varies depending on the type and amount of the harmful organism, cultivation form, or growing condition of the target crop or tree, in general, 0.1 to 1000 g, preferably 1 to 100 g, of the active ingredient is applied per 10 ares. In this case, a water dispersible powder, a granular water dispersible powder, a dry flowable agent, a water soluble agent, an emulsion agent, a liquid agent, a flowable agent such as a suspension agent in water or an emulsion agent in water, or capsules is diluted with water and, while it varies depending on the type, cultivation form, or growing condition of the target plant, in general, the diluted formulation may be sprayed to a crop or the like in an application amount of 10 to 1000 L per 10 ares. In case of a powder formulation, a spray formulation, or an aerosol formulation, a crop or the like may be treated with the formulation as its state.

Examples of the application method when the target harmful organisms mainly harm plants in the soil or when the target harmful organisms are controlled by allowing a chemical agent to be absorbed from the roots include a method of applying a formulation to the plant root or nursery bed for raising seedling with or without dilution in water, a method of spraying granules to the plant root or the nursery bed for seedling, a method of spraying a powder formulation, a water dispersible powder, a granular water dispersible powder, or granules to mix them with the whole soil before sowing or transplanting, and a method of spraying a powder formulation, a water dispersible powder, a granular water dispersible powder, granules, or fine granules to the planting holes or planting rows before sowing or planting plants. It is sufficient that a water dispersible powder, a granular water dispersible powder, a water-soluble agent, an emulsion agent, a liquid agent, a flowable agent such as a suspension agent in water or an emulsion agent in water, or capsules is diluted with water and may be sprayed to the soil surface or irrigated into soil, in general, in an application amount of 5 to 500 L per 10 ares, so as be uniform in the entire treatment area. A powder formulation, granules, fine granules, or a bait may be sprayed to the soil surface in the state of the formulation so as be uniform in the entire treatment area. The spraying or irrigation may be performed around the seeds, crops, or trees to be protected from harm. In addition, the active ingredient may be mechanically dispersed by plowing during spraying or after spraying.

As the method of application to the paddy rice nursery box, while the dosage form may differ depending on the time of application, such as application at the time of sowing, application at the greening stage, or application at the time of transplantation, for example, application may be performed in a dosage form such as a powder formulation, a granular water dispersible powder, granules, or fine granules. Application can be also performed by mixing the formulation with culture soil, and culture soil may be mixed with a powder formulation, a granular water dispersible powder, granules, or fine granules by, for example, bed soil mixing, cover soil mixing, or mixing with the entire culture soil. Alternatively, simply, culture soil and a formulation may be alternately applied in a layer form.

As the method of application to a paddy field, in general, a solid formulation such as a jumbo agent, a pack agent, granules, or a granular water dispersible powder or a liquid agent such as a flowable agent or an emulsion agent is sprayed to a paddy field in a submerged condition. In addition, at the time of planting rice, an appropriate formulation can also be sprayed to or injected in soil directly or as a mixture with a fertilizer. Use of a liquid chemical agent, such as an emulsion agent or a flowable agent, at a source of water inflow to a paddy field, such as a water outlet or irrigation equipment allows application with the supply of water in a labor-saving manner.

Examples of the method of seed treatment include a method of immersing seeds in a liquid or solid formulation in a liquid state with or without diluting to allow the chemical to attach to or infiltrate into the seeds, a method of mixing a solid formulation or a liquid formulation with seeds for dressing treatment to allow the formulation to adhere to the surfaces of the seeds, a method of mixing seeds with an adhesive carrier, such as a resin or a polymer, to coat the seeds with the carrier, and a method of spraying a formulation near seeds at the same time as planting. The term "seeds" to be subjected to seed treatment means early cultivated plant bodies used for plant propagation, and examples thereof include, in addition to seeds, bulbs, tubers, seed potatoes, shoots, propagules, and vegetative propagation plants for bulb or cutting cultivation. The term "soil" or "cultivation carrier" for a plant in application indicates a support for cultivating a crop, in particular, a support for allowing roots to grow, and the material thereof is not particularly limited as long as it allows plants to grow. The support may be so-called soil, nursery mat, or water, and the examples of the material include sand, pumice, vermiculite, diatomaceous earth, agar, gel-like substance, polymer substance, rock wool, glass wool, wood chips, and bark.

Treatment of a cultivated plant to be transplanted in sowing and raising of seeding period is preferably direct treatment of seeds or irrigation treatment of a chemical agent in a liquid state or spraying treatment of granules to a nursery bed. In addition, treatment of planting holes with granules at the time of planting or mixing granules with the cultivation carrier near the transplantation position is also preferable.

The compound of the present invention represented by the formula (1) is also valuable for protecting wood (standing trees, fallen trees, processed timber, stored timber, or structural timber) from harm of insects, such as termites and beetles, and fungi. In such a situation, the controlling is possible by a method of performing spraying, injection, irrigation, or application of an oil agent, an emulsion agent, a water dispersible powder, a sol formulation or spraying of a powder formulation or granules to the wood or the soil around the wood. The oil agent, the emulsion agent, the water dispersible powder, or the powder formulation that is used in this situation can be present as a mixed agent with another active compound, such as an insecticide, a miticide, a nematicide, a fungicide, a repellent, or a synergist, and the total amount of active ingredient compounds in such a formulation is 0.0001 to 95 mass %. For the oil agent, the powder formulation, or the granules, the amount is preferably 0.005 to 10 mass %, and for the emulsion agent, the water dispersible powder, or the sol formulation, the amount is preferably 0.01 to 50 mass %. In cases of controlling arthropods or fungi, 0.01 to 100 g of the active ingredient compound is sprayed per 1 $m^2$ of soil or wood surface.

The compound of the present invention represented by the formula (1) can be used for protecting products of, for example, cereals, fruits, nuts, spices, and tobacco when they are stored as they are, in powdered forms, or in mixed states in products, from harm by Lepidoptera, Coleoptera, mites, and fungi. Also, when animal products (leather, fur, wool, feather, etc.) or plant products (cotton, paper, etc.) are stored in their natural or converted states, it is possible to protect them from attacks of *Lepidoptera, Coleoptera, Thysanura,* and *Periplaneta.* Furthermore, it is possible to protect foods such as meat and fish from attack by Lepidoptera, Coleoptera, Diptera, and mites. In such a situation, controlling is possible by a method of spraying an oil agent, an emulsion agent, a water dispersible powder, or a powder formulation, installing a resin transpiration agent, treating with a smoking agent or a haze formulation, installing granules, tablets, or a poison bait, or spraying aerosol. These formulations can also be present as a mixed agent with another active compound, such as an insecticide, a miticide, a nematicide, a fungicide, a repellent, or a synergist, and the total amount of the active ingredient compounds in such a formulation can be 0.0001 to 95 mass %.

The compound of the present invention represented by the formula (1) is valuable for exterminating or preventing arthropods or fungi that parasitize the body surface of humans and livestock and cause direct harm such as skin feeding or blood sucking; arthropods, nematodes, trematodes, cestodes, or protozoans that spread human and livestock diseases or are mediators of such diseases; and arthropods that make humans uncomfortable. In such a situation, the compound of the present invention can be orally administered as a meal or feed containing a small amount of the compound of the present invention or as an appropriate ingestible pharmaceutical chemical composition, for example, tablets, pills, capsules, pastes, gels, beverages, medicated feeds, medicated drinking water, medicated baits, or controlled release large pills including a pharmaceutically acceptable carrier or coating material, or another controlled release device to be retained in the gastrointestinal tract, or can be percutaneously administered as spray, powder, grease, cream, ointment, emulsion, lotion, a spot-on agent, a pore-on agent, or shampoo. In order to achieve an effect by such uses, the formulation generally contains 0.0001 to 0.1 mass %, preferably 0.001 to 0.01 mass %, of an active ingredient compound. Incidentally, as the method for percutaneous administration or topical administration, a device (for example, a collar, medallion, or ear tag) attached to an animal can be used for controlling arthropods locally or systemically.

An oral administration method and a transdermal administration method when the compound of the present invention represented by the formula (1) is used as an insecticide for animals such as livestock and pets or humans will now be specifically explained but is not limited thereto.

When the compound is orally administered as a medicated drinking water, the beverage is usually a solution, suspension, or dispersion of the compound in an appropriate nontoxic solvent or water together with a suspension agent, such as bentonite, or a humectant or another excipient. In general, a beverage also contains an antifoam agent. A beverage formulation generally contains 0.01 to 1.0 mass %, preferably 0.01 to 0.1 mass %, of an active ingredient compound.

When it is desirable to orally administer a dry solid in a unit dosage form, generally, capsules, pills, or tablets containing a predetermined amount of an active ingredient are used. These use forms are manufactured by mixing an active ingredient with an appropriately finely crushed diluent, filler, disintegrant, and/or binder, such as starch, lactose, talc, magnesium stearate, or vegetable rubber. Such a unit use prescription can widely change the mass and content of an insecticide according to the type of the host animal to be treated, the degree of infection, the type of the parasite, and the weight of the host.

In administration through animal feed, the active compound can be used by being homogeneously dispersed in the feed, as top dressing, or in a form of pellet. In general, in order to achieve a desirable antiparasitic effect, the final content of the active ingredient compound in feed is 0.0001 to 0.05 mass % and preferably 0.0005 to 0.01 mass %.

The active compound to be dissolved or dispersed in a liquid carrier excipient can be parenterally administered to an animal by intragastric, intramuscular, intratracheal, or subcutaneous injection. For parenteral administration, 10 the active compound is suitably mixed with appropriate vegetable oil, such as peanut oil or cottonseed oil. In such a prescription, generally, the content of the active ingredient compound is 0.05 to 50 mass % and preferably 0.1 to 5.0 mass %.

Alternatively, the active compound can be topically administered by mixing it with an appropriate carrier, such as dimethyl sulfoxide or a hydrocarbon solvent. This formulation is directly applied to the animal outer surface by spray or direct addition.

In addition, the compound of the present invention represented by the formula (1) can also be used as an insecticide against arthropods that cause direct harm or arthropods that are mediators of disease, by spraying, injecting, irrigating, or applying an oil agent, an emulsion 25 agent, a water dispersible powder, etc., by spraying a powder formulation, etc., by treatment with a fumigant, a heat haze formulation such as a mosquito coil, self-burning smoking agent, or a chemical reaction-type haze formulation, a smoking agent such as fogging, or a ULV agent, or by installation of granules, tablets, or a poison bait in the surrounding environment where the harmful organisms may be latent, or by addition by dropping a floating powder formulation, granules, etc. in a water channel, a well, a water reservoir, a water tank, or another running or stagnant water. Furthermore, Lymantriidae, which is also an agricultural and forest pest, can be controlled by the same method as above. Against Diptera, a method of mixing the compound with feed of livestock so that the compound is mixed with feces is effective, and against Culicidae, a method of volatilizing the compound in the air with an electric mosquito-repellent device or the like is also effective. Incidentally, the formulations in these use forms can be present as mixed agents with another active compound, such as a pest control agent, a mite control agent, a nematode control agent, a disease control agent, a repellent, or a synergist, and the total amount of the active ingredient compounds in such a formulation is 0.0001 to 95 mass %.

The compound of the present invention represented by the formula (1) can also be present together with another active compound as a mixing agent. In particular, in control of harmful organisms, such as arthropods, gastropods, and nematodes, that damage plants, the range of the objective pests to be controlled can be expanded by using the compound as a mixture with a compound (insecticide) having a pest-controlling activity, a tick-controlling activity, or a nematode-controlling activity, and synergistic effects, such as a reduction in dosage, can be expected. Examples of such an active compound include the followings.

Organophosphorus agents, such as acephate, azinphosmethyl, chlorpyrifos, daizinon, dichlorvos, dimeton-S-methyl, dimethoate, dimethylvinphos, disulfoton, ethion, fenitrothion, fenthion, isoxathion, malathion, methamidophos, methidathion, monocrotophos, naled, oxideprofos, parathion, phenthoate, phosalone, pirimiphos-methyl, piridafenthion, profenofos, prothiofos, propaphos, pyraclofos, salithion, sulprofos, thiometon, tetrachlorvinfos, trichlorphon, and vamidothion;

Carbamate agents, such as alanycarb, bendiocarb, benfuracarb, carbaryl, carbofuran, carbosulfan, ethiofencarb, fenobucarb, furathiocarb, isoprocarb, methomyl, metolcarb, pirimicarb, propoxur, and thiodicarb;

Organic chlorine agents, such as aldrin, chlordane, DDT (p,p'-DDT), endosulfan, and lindane;

Pyrethroid agents, such as acrinathrin, allethrin, bifenthrin, cycloprothrin, cyfluthrin, cyhalothrin, cyphenothrin, cypermethrin, deltamethrin, ethofenprox, fenpropathrin, fenvalerate, flucythrinate, flufenprox, fluvalinate, furamethrin, halfenprox, imiprothrin, permethrin, phenothrin, prallethrin, pyrethrins, resmethrin, silafluofen, tefluthrin, tralomethrin, and transfluthrin; Neonicotinoid agents, such as acetamiprid, clothianidin, dinotefran, imidacloprid, nitenpyram, thiacloprid, and thiamethoxam;

Diamide agents, such as chlorantraniliprole, cyantraniliprole, cyclaniliprole, flubenziamide, and tetraniliprole;

Phenylpyrazole agents, such as ethiprole, fipronil, acetoprole, pyrafluoprole, and pyriplore;

Nereistoxin agents, such as bensultap, cartap, thiocyclam, and thiosultap;

Insect growth regulators including phenyl benzoyl urea agents and diacylhydrazines, such as chlorfluazuron, diflubenzuron, flufenoxuron, hexaflumuron, lufenuron, novaluron, teflubenzuron, triflumuron, buprofezin, chromafenozide, halofenozide, methoxyfenozide, tebufenozide, and cyromazine;

Juvenile hormone agents, such as diofenolan, fenoxycarb, hydroprene, methoprene, and pyriproxyfen;

Insecticidal materials produced by microorganisms, such as abamectin, emamectin-benzoate, ivermectin, lepimectin, milbemectin, nemadectin, Nikkomycin, polioxins, spinetram, spinosad, and BT agents;

Insecticidal materials derived from natural products, such as anabasine, azadiractin, deguelin, decanolyoctanoylglycerol, hydroxy propyl starch, soybean lecithin, nicotine, nornicotine, sodium oleate, petroleum oil, propylene glycol fatty acid ester (propylene glycol monolaurate), rape oil, rotenone, sorbitan fatty acid ester, and starch;

Other insecticides, such as afidpyropen, benzpyrimoxan, broflanilide, chlorfenapyr, diafenthiuron, dicloromezotiaz, dimpropyridaz, DBEDC (dodecyl benzene sulphonic acid bisethylenediamine copper [II] salt), flonicamid, flometoquin, flufenerim, flupyradifurone, flupyrimin, fluralaner, fluhexafon, fluxametamide, hydramethylnon, indoxacarb, isocycloseram, metaflumizone, metaldehyde, nicotin sulfate, oxazosulfyl, pymetrozine, pyridalyl, pyrifluquinqzon, spirotetramat, sulfoxaflor, tolfenpyrad, triazamate, triflumezopyrim, and tyclopyrazoflor;

Miticides, such as acequinocyl, acynonapyr, amidoflumet, amitraz, azocyclotin, benzoximate, bifenazate, binapacryl, bromopropylate, chinomethionat, clofentezine, cyenopyrafen, cyflumetofen, tricyclohexyltin hydroxide (cyhexatin), dicofol, dienochlor, ethoxazole, fenazaflor, fenazaquin, fenbutatin oxide, fenothiocarb, fenpyroximate, fluacrypyrim, hexythiazox, pirimidifen, polynactins, propargite, pyflubumide, pyridaben, spirodiclofen, spiropidion, spiromesifen, tebufenpyrad, tetradifon, and KUI-1821 (test name);

Nematicides, such as aluminum phosphide, benclothiaz, cadusafos, ethoprophos, fluazaindolizine, fluensulfone, fosthiazate, furfural, imicyafos, levamisol hydrochloride, mesulfenfos, carbam (metam-ammonium), methyl isothiocyanate, morantel tartrate, oxamyl, and thioxazafen; and Poison baits, such as chlorphacinone, coumatetralyl, diphacinone, monofluoroacetate (sodium fluoracetate), and warfarin.

The compound of the present invention represented by the formula (1) can also be present as a mixed agent with an active compound other than the compound having a pest-controlling activity, a tick-controlling activity, or a nematode-controlling activity. In order to control diseases and/or weeds that simultaneously occur in the time of use, a synergistic effect of a reduction in pest control labor and a reduction in dosage can be expected by using the compound of the present invention in combination with a compound having a bactericidal activity, an herbicidal activity, or a plant growth regulating activity. In addition, a more effective control effect by the synergistic effect, etc. can be expected by using the compound mixed with a repellent or a synergist.

Examples of such an active compound include disease control agents, for example, D-D (1,3-dichloropropene), acibenzolar-S-methyl, aldimorph, ametoctradin, amisulbrom, andoprim, triazine (anilazine), azaconazole, azoxystrobin, basic copper sulfate, benodanil, benomyl, benthiavalicarb-isopropyl, benthiazole, bitertanol, bixafen, blasticidin S, boscalid, bromuconazole, calcium carbonate, buthiobate, lime sulfur (calcium polysulfide), captafol, captan, carbendazim, carboxin, carpropamid, chinomethionat, chlorfenazole, chloroneb, chloropicrin, chlorothalonil, chlozolinate, DBEDC (complex of bis(ethylenediamine)copper-bis-(dodecylbenzenesulfonic acid)), copper hydroxide, copper nonylphenol sulfonate, copper oxychloride, cyazofamid, 25 cyflufenamid, cymoxanil, cyproconazole, cyprodinil, dazomet, diclobutrazol, dichlofluanid, dichlone, diclocymet, diclomezine, diethofencarb, difenoconazole, diflumetorim, dimethomorph, dimoxystrobin, diniconazole, diniconazole-M, dithane-stainless, dithianon, dodine, echlomezole, edifenphos, enestrobin, epoxiconazole, etaconazole, ethaboxam, extract from mushroom, famoxadone, fenamidone, fenarimol, fenbuconazole, fenfuram, fenhexamid, fenoxanol, fenpiclonil, fenpropidin, fenpyrazamine, ferimzone, fluazinam, flumetover, flumorph, fluopicolide, fluopyram, fluoroimide, fluotrimazole, fluoxastrobin, fluquinconazole, flusulfamide, flutolanil, fluxapyroxad, folpet, fosetyl-Al, fthalide, fuberidazole, fludioxonil, flusilazole, flutianil, flutriafol, furametpyr, furconazole, guazatine, hexaconazole, hydroxyioxazole, hymexazol, imazalil, imazalil sulfate, imibenconazole, iminoctadine acetate, iminoctadine-albesilate (iminoctadine-DBS), ipconazole, IBP (iprobenfos), iprodione, iprovalicarb, isofetamid, isoprothiolane, isopyrazam, isotianil, kasugamycin, kresoxim-methyl, mancozeb, mandipropamid, maneb, manzeb, mepanipyrim, mepronil, metalaxyl, carbam (metam-ammonium), carbam-sodium (metam-sodium), metconazole, methasulfocarb, methyl bromide, methylisothiocyanate, metominostrobin, metrafenone, mildiomycin, myclobutanil, organic sulfur nickel salt (nickel dimethyldithiocarbamate), nuarimol, orysastrobin, oxadixyl, oxathiapiprolin, organocopper (oxine-copper), oxolinic acid, oxpoconazole fumarate, oxycarboxin, oxytetracycline, pebulate, pefurazoate, penconazole, pencycuron, penflufen, penthiopyrad, picarbutrazox, picoxystrobin, piperalin, polycarbamate, polyoxin-B, polyoxins, potassium hydrogen carbonate, probenazole, prochloraz, procymidone, propamocarb, propiconazole, propineb, proquinazid, prothioconazole, pyraclostrobin, pyrametostrobin, pyraoxystrobin, pyrazophos, pyribencarb, pyridinitril, pyrifenox, pyrimethanil, pyriofenone, pyroquilon, quinoxyfen, quintozene, sedaxane, silver, simeconazole, sodium hydrogen carbonate, sodium hypochlorite, spiroxamine, streptomycin, sulfur, tebfloquin, tebuconazole, tecloftalam, terbinafine, tetraconazole, thiabendazole, thiadiazin, thifluzamide, thiophanate, thiophanate-methyl, thiram, tiadinil, tolclofos-methyl, tolprocarb, tolylfluanid, triadimefon, triadimenol, triclopyricarb, tricyclazole, tridemorph, trifloxystrobin, triflumizole, triforine, triticonazole, uniconazole-P, validamycin(-A), vinclozolin, zarilamid, zinc sulfate, zineb, ziram, and zoxamide.

Examples of the compound having an herbicidal activity include aclonifen, acifluofen n-sodium, alachlor, alloxydim, amicarbazone, amidosulfuron, anilofos, asulam, atrazine, azimsulfuron, benfuresate, bensulfuron-methyl, bentazone, benthiocarb, benzobicyclon, benzofenap, bialaphos, bifenox, bromobutide, bromoxynil, butamifos, cafenstrole, calcium peroxide, carbetamide, cinosulfuron, clomeprop, cyclosulfamuron, cyhalofop-butyl, daimuron, desmedipham, diclofop-methyl, diflufenican, dimefuron, dimethametryn, dinoterb, diquat, diuron, esprocarb, ethiozin, ethofumesate, ethoxysulfuron, etobenzanid, fenoxaprop-P-ethyl, fentrazamide, flucarbazone, flufenacet, flurtamone, fluthiacet-methyl, foramsulfuron, glufosinate-ammonium, glyphosate-isopropyl amine, glyphosate-trimesium, imazapyr, imazosulfuron, indanofan, iodosulfuron, ioxynil-octanoate, isoproturon, isoxadifen, isoxaflutole, lactofen, linuron, mefenacet, mesosulfuron, metamitron, methabenzthiazuron, metosulam, metribuzin, napropamide, neburon, oxadiargyl, oxadiazon, oxaziclomefone, paraquat, pendimethalin, pentoxazone, phenmedipham, pretilachlor, propoxycarbazone, prosulfocarb, pyraclonil, pyraflufen-ethyl, pyrazolate, pyrazosulfuron n-ethyl, pyributicarb, pyriftalid, pyriminobac-methyl, quizalofop-ethyl, sethoxydim, simazine, sulcotrion, sulfentrazone, thenylchlor, triaziflam, and tribufos.

As the compound having a plant growth regulating activity, for example, 1-naphthylacetamide (1-naphthylacetic acid), 4-CPA, 6-benzylaminopurine, butralin, calcium chloride, calcium formate, calcium peroxide, calcium sulfate, chlormequat (chlormequat chloride), choline, cyanamide, cyclanilide, daminozide, decyl alcohol, dichlorprop, ethephon, ethychlozate, flurprimidol, forclorfenuron, gibberellin (gibberellic acid), indolebutyric acid, maleic hydrazide potassium salt, mefenpyr, mepiquat chloride, oxine sulfate (8-hydroxyquinoline sulfate), paclobutrazol, paraffin, prohexadione-calcium, prohydrojasmon, thidiazuron, trinexapac-ethyl, uniconazole-P, or wax can be used in combination.

Examples of the repellent include capsaicin, carane-3,4-diol, citronellal, deet, dimethyl phthalate, hinokitiol, limonene, linalool, menthol, menthone, naphthalene, and thiram.

Examples of the synergist include methylenedioxynaphthalene, naphthyl propynyl ether, nitrobenzyl thiocyanate, octachlorodipropyl ether, pentynyl phthalimide, phenyl salioxon, piperonil butoxide, safrole, sesamex, sesamin, sulfoxide, triphenyl phosphate, and verbutin.

The compound of the present invention is expected to provide the same effect as that of a biotic pesticide by being used in combination with the biotic pesticide, for example, a viral formulation, such as Cytoplasmic polyhedrosis virus (CPV), Entomopox virus (EPV), Granulosis virus (GV), or Nuclear polyhedrosis virus (NPV); a microbial pesticide that is used as an insecticide or a nematicide, such as *Beauveria bassiana, Beauveria brongniartii, Monacrosporium phymatophagum, Paecilomyces fumosoroseus, Pasteuria penetrans, Steinernema carpocapsae, Steinernema glaseri, Steinernema kushidai,* or *Verticillium lecanii*; a microbial pesticide that is used as a fungicide, such as *Agrobacterium radiobactor, Bacillus subtilis,* nonpathogenic *Erwinia carotovora,* nonpathogenic *Fusarium oxysporum, Pseudomonas* CAB-02, *Pseudomonas fluorescens, Talaromyces flavus, Trichoderma atroviride,* or *Trichoderma lignorum*; or a biotic pesticide that is used as an herbicide, such as *Xanthomonas campestris.*

Furthermore, it is possible to use the present compound as a biotic pesticide in combination with, for example, a natural enemy, such as *Amblyseius californicus, Amblyseius cucumeris, Amblyseius degenerans, Aphidius colemani, Aphidoletes aphidimyza, Chrysoperia carnea, Dacnusa sibirica,*

*Diglyphus isaea, Encarsia formosa, Eretmocerus eremicus, Franklinothrips vespiformis, Harmonia axyridis, Hemiptarsenus varicornis, Neochrysocharis formosa, Orius sauteri, Orius strigicollis, Phytoseiulus persimilis, Pilophorus typicus,* or *Piocoris varius*; or a pheromone formulation, such as codlelure, cuelure, geraniol, gyptol, liblure, looplure, methyl eugenol, orfralure, peachflure, phycilure, pyrimalure, or turpentine.

EXAMPLES

The present invention will now be further described in detail by Examples, Formulation Examples, and Test Examples, but the scope of the present invention is not limited to these Examples, Formulation Examples, and Test Examples.

Example 1. Synthesis of N-(methoxymethyl)-N-{4-(trifluoromethyl)phenyl}-3-(ethylthio)-6-(trifluoromethyl)imidazo[1,2-a]pyridine-2-carboxamide Compound No.: A-13)

Sodium hydride (60%, 0.06 g) was added to a solution of N-{4-(trifluoromethyl)-3-(ethylthio)-6-(trifluoromethyl) imidazo[1,2-a]pyridine-2-carboxamide (0.35 g) in N,N-dimethylformamide (3.5 mL), followed by stirring at room temperature for 6 minutes. Chloromethyl methyl ether (122 µL) was then added thereto, followed by stirring at room temperature for 3.5 hours. Furthermore, chloromethyl methyl ether (122 µL) was added thereto, followed by stirring at room temperature for 2.5 hours. After addition of 1 N hydrochloric acid to the reaction solution, extraction with ethyl acetate was performed. The resulting organic layer was washed with saturated saline solution and was then dried over anhydrous sodium sulfate. The desiccant was filtered off, and the solvent was distilled under reduced pressure. The residue was purified by silica gel column chromatography to obtain N-(methoxymethyl)-N-{4-(trifluoromethyl)phenyl}-3-(ethylthio)-6-(trifluoromethyl)imidazo[1,2-a]pyridine-2-carboxamide (0.27 g, mp: 103° C. to 105° C.)

Example 2. Synthesis of N-(methoxymethyl)-N-{4-(trifluoromethyl)phenyl}-3-(ethylsulfinyl)-6-(trifluoromethyl)imidazo[1,2-a]pyridine-2-carboxamide (Compound No.: A-14)

3-Chloroperbenzoic acid (0.06 g) was added to a solution of N-(methoxymethyl)-N-{4-(trifluoromethyl)phenyl}-3-(ethylthio)-6-(trifluoromethyl)imidazo[1,2-a]pyridine-2-carboxamide (0.11 g) in chloroform (2 mL), followed by stirring at room temperature for 3.5 hours. Saturated sodium bicarbonate water was added to the reaction solution, followed by extraction with chloroform. The resulting organic layer was washed with saturated saline solution and was then dried over anhydrous sodium sulfate. The desiccant was filtered off, and the solvent was distilled under reduced pressure. The resulting crude crystals were washed with hexane to obtain N-(methoxymethyl)-N-{4-(trifluoromethyl)phenyl}-3-(ethylsulfinyl)-6-(trifluoromethyl) imidazo[1,2-a]pyridine-2-carboxamide (0.08 g, mp: 147° C. to 149° C.).

Example 3. Synthesis of N-(methoxymethyl)-N-{4-(trifluoromethyl)phenyl}-3-(ethylsulfonyl)-6-(trifluoromethyl) imidazo[1,2-a] pyridine-2-carboxamide (Compound No.: A-15)

3-Chloroperbenzoic acid (0.27 g) was added to a solution of N-(methoxymethyl)-N-{4-(trifluoromethyl)phenyl}-3-(ethylthio)-6-(trifluoromethyl)imidazo[1,2-a]pyridine-2-carboxamide (0.22 g) in chloroform (3 mL), followed by stirring at room temperature for 4 hours. Saturated sodium bicarbonate water was added to the reaction solution, followed by extraction with chloroform. The resulting organic layer was washed with saturated saline solution and was then dried over anhydrous sodium sulfate. The desiccant was filtered off, and the solvent was distilled under reduced pressure. The resulting crude crystals were washed with hexane to obtain N-(methoxymethyl)-N-{4-(trifluoromethyl)phenyl}-3-(ethylsulfonyl)-6-(trifluoromethyl)imidazo[1,2-a]pyridine-2-carboxamide (0.22 g, mp: 165° C. to 166° C.).

Regarding compounds manufactured as in the above Examples, the $^1$H-NMR data are shown in the following Table 2.

TABLE 2

| Compound No. | 1H-NMR [CDCl3/TMS, 400 MHz] |
|---|---|
| A-1 | 1H-NMR(CDCl3)δppm: 1.22 (3H, t), 2.32(3H, s), 3.74(2H, s), 5.39(2H, br), 7.42(3H, d), 7.50(2H, d), 7.62(1H, d), 8.71(1H, s) |
| A-4 | 1H-NMR(CDCl3)δppm: 1.19(3H, t), 1.21(3H, t), 2.82(2H, q), 3.74(2H, s), 5.37(2H, s), 7.40(3H, d), 7.49(2H, d), 7.61(2H, d), 8.74(1H, s) |
| A-7 | 1H-NMR(CDCl3)δppm: 0.97(3H, t), 1.22(3H, t), 1.53(2H, q), 2.74(2H, t), 3.75(2H, s), 5.37(2H, s), 7.40(3H, d), 7.49(2H, d), 7.61(1H, d), 8.72(1H, s) |
| A-10*[1] | 1H-NMR(CDCl3)δppm: 1.22-1.24(9H, m), 3.44 + 3.59(1H, quin + quin), 3.75 + 3.83(2H, s + q), 5.36 + 5.63(2H, s + s), 7.40-7.81(6H, m), 8.75 + 8.92(1H, s + s) |
| A-12*[1] | 1H-NMR(CDCl3)δppm: 1.10 + 1.21(3H, s + t), 1.38(6H, d), 3.54 + 3.85-3.94(4H, s + m), 5.13 + 5.36(2H, s + s), 7.40-8.06(6H, m), 9.22 + 9.36(1H, s + s) |
| A-16 | 1H-NMR(CDCl3)δppm: 1.18-1.28(6H, m), 2.86(2H, q), 3.79(2H, s), 5.32(2H, s), 7.28-7.95(7H, m) |
| A-21*[1] | 1H-NMR(CDCl3)δppm: 1.11 + 1.24(3H, s + t), 1.35 + 1.41(3H, t + t), 3.60 + 3.84(4H, q + q), 5.17 + 5.36(2H, s + s), 7.19(1H, d), 7.51 + 7.73(4H, s + s), 7.83 + 8.12(1H, s + s), 9.02 + 9.15(1H, d + d) |
| A-22*[1] | 1H-NMR(CDCl3)δppm: 1.18 + 1.21(6H, t + br), 2.87 + 2.94(2H, q + q), 3.74 + 3.83(2H, s + q), 5.39 + 5.63(2H, s + s), 6.98 + 7.06(1H, t + t), 7.42-7.60(5H, m), 8.59 + 8.73(1H, d + d) |

TABLE 2-continued

| Compound No. | 1H-NMR [CDCl3/TMS, 400 MHz] |
|---|---|
| A-24*[1] | 1H-NMR(CDCl3)δppm: 1.12-1.29(3H, m), 1.35 + 1.41(3H, t + t), 3.60 + 3.84(4H, q + q), 5.17-5.27 + 5.36(2H, m + s), 7.07(1H, t), 7.26-8.06(5H, m), 9.06 + (1H, d + s) |
| A-25 | 1H-NMR(CDCl3)δppm: 1.18(6H, m), 2.77(2H, q), 3.73(2H, s), 5.37(2H, s), 7.22(1H, d), 7.39-7.50(5H, m), 8.41(1H, s) |
| A-28 | 1H-NMR(CDCl3)δppm: 1.17-1.24(6H, m), 2.37(2H, s), 2.74(2H, q), 3.71(2H, d), 5.39(2H, s), 7.11(1H, d), 7.42-7.50(5H, m), 8.16(1H, s) |
| A-29*[1] | 1H-NMR(CDCl3)δppm: 1.18 + 1.24(3H, t + t), 2.36(3H, s), 3.24-3.33(1H, m), 3.42-3.55(1H, m), 3.56 + 3.68 + 3.86(2H, d + t + s), 5.28-5.36 + 5.81(2H, m + br), 7.19(1H, d), 7.43(3H, d), 7.59(2H + d), 8.64 + 9.00(1H, s + s) |
| A-31 | 1H-NMR(CDCl3)δppm: 1.19(3H, t), 1.24(3H, t), 2.81(2H, q), 3.76(2H, s), 5.37(2H, 2), 7.39-7.42(4H, m), 7.60(2H, s), 8.72(1H, s) |
| A-33*[1] | 1H-NMR(CDCl3)δppm: 1.27(3H, t), 1.36(3H, t), 3.54 + 3.85(4H, q + q), 5.13 + 5.36(2H, s + s), 7.29-8.05(6H, m), 9.22 + 9.40(1H, s + s) |
| A-34*[1] | 1H-NMR(CDCl3)δppm: 1.04 + 1.18-1.23 + 1.27(6H, t + m + t), 2.87-3.03(2H, m), 3.20-4.00(2H, m), 4.58 + 4.75(1H, d + d), 5.79 + 6.08(1H, d + d), 7.28-7.83(6H, m), 8.77 + 8.92(1H, s + s) |
| A-43 | 1H-NMR(CDCl3)δppm: 1.18(3H, t), 1.27(3H, t), 2.21(3H, s), 2.74(2H, s), 3.86(2H, s), 5.34(2H, s), 6.95(2H, s), 7.11(2H, s), 7.37(1H, s), 7.60(1H, s), 8.64(1H, s) |
| A-46 | 1H-NMR(CDCl3)δppm: 1.19(3H, t), 1.27(3H, s), 2.81(2H, s), 3.86(2H, s), 5.33(2H, s), 6.85(2H, s), 7.21(2H, s), 7.39(1H, s), 7.58(1H, s), 8.66(1H, s) |
| A-49 | 1H-NMR(CDCl3)δppm: 1.19(3H, t), 1.26(3H, t), 2.81(2H, s), 3.81(2H, s), 5.33(2H, s), 7.19(4H, s), 7.39(1H, d), 7.61(1H, s), 8.70(1H, s) |
| A-52 | 1H-NMR(CDCl3)δppm: 1.18(3H, t), 1.24(3H, t), 2.81(2H, d), 3.80(2H, s), 5.33(2H, s), 7.15(2H, s), 7.32-7.42(3H, m), 7.61(1H, d), 8.71(1H, s) |
| A-55 | 1H-NMR(CDCl3)δppm: 1.18(3H, t), 1.24(3H, t), 2.80(2H, d), 3.78(2H, s), 5.33(2H, s), 7.02(2H, s), 7.40(1H, d), 7.52(2H, s), 7.62(1H, d), 8.71(1H, s) |
| A-61*[1] | 1H-NMR(CDCl3)δppm: 1.20-1.29(6H, m), 2.85 + 2.96(2H, q + q), 3.71 + 3.84(2H, q + q), 5.38 + 5.64(2H, s + s), 7.38-7.83(6H, m), 8.76 + 8.92(1H, s + s) |
| A-63*[1] | 1H-NMR(CDCl3)δppm: 1.24 + 1.37(6H, t + t), 3.58 + 3.74-3.85(4H, q + m), 5.35(2H, s), 7.40-8.06(6H, m), 9.28 + 9.66(1H, s + s) |
| A-67 | 1H-NMR(CDCl3)δppm: 1.19(3H, t), 2.83(2H, s), 3.81(2H, s), 5.34(2H, s), 7.00(2H, s), 7.30-7.42(3H, m), 7.60(1H, s), 8.72(1H, s) |
| A-68*[1] | 1H-NMR(CDCl3)δppm: 1.22(3H, s), 1.42(3H, t), 3.30-3.39 + 3.43-3.51 + 3.69(4H, m + m + s), 5.17 + 5.39 + 6.10(2H, s + d + s), 7.20 + 7.42 + 7.78(6H, s + s + s), 9.67(1H, s) |
| A-69*[1] | 1H-NMR(CDCl3)δppm: 1.09 + 1.26(3H, t + t), 1.24 + 1.36(3H, t + t), 3.56 + 3.84(4H, q + q), 5.11 + 5.34(2H, s + s), 7.04 7.31(2H, d + d), 7.41 + 7.50(2H, d + d), 7.52 + 7.69(2H, d + d), 7.63 + 7.92(2H, d + d), 9.25 + 9.40(1H, s + s) |
| A-70*[1] | 1H-NMR(CDCl3)δppm: 1.19 + 1.22 + 1.46(6H, t + t + t), 2.80 + 2.96(2H, q + q), 3.74 + 4.49(2H, d + q), 5.38(2H, s), 7.32-7.83(6H, m), 8.74 + 8.91(2H, s + s) |
| A-71 | 1H-NMR(CDCl3)δppm: 1.21(3H, t), 1.43(3H, t), 3.31-3.40(1H, m), 3.43-3.52(1H, m), 3.61(1H, s), 3.70(1H, s), 5.29(1H, s), 5.71(1H, br), 7.35(2H, s), 7.46(2H, s), 7.63(2H, d), 9.72(1H, s) |
| A-72*[1] | 1H-NMR(CDCl3)δppm: 1.14 + 1.26 + 1.37(6H, s + s + t), 3.60 + 3.85(4H, q + d), 5.16 + 5.37(2H, s + s), 7.42 + 8.07(6H, m), 9.27 + 9.37(1H, s + s) |
| A-75 | 1H-NMR(CDCl3)δppm: 1.27 + 1.37(6H, s + t), 3.60 + 3.85(4H, q + s), 5.39(2H, s), 7.40-8.06(6H, m), 9.28(1H, s) |
| A-79 | 1H-NMR(CDCl3)δppm: 1.21-1.30(6H, m), 2.88(2H, q), 3.68(2H, q), 5.43(2H, s), 7.43(1H, d), 7.57(3H, d), 7.89(2H, d), 8.79(1H, s) |
| A-80*[1] | 1H-NMR(CDCl3)δppm: 1.23 + 1.44(6H, t + t), 3.33-3.42(1H, m), 3.44-3.51(1H, m), 3.56-3.61(1H, m), 3.66-3.80(1H, m), 5.28(1H, d), 5.82(1H, d), 6.71-8.09(6H, m), 9.74(1H, s) |
| A-81*[1] | 1H-NMR(CDCl3)δppm: 1.24 + 1.38 + 1.47(6H, t + t + t), 3.61 + 3.73 + 3.79(4H, q + q + s), 4.51 + 5.38(2H, q + s), 7.59-7.72(4H, m), 7.92-7.95(2H, m), 9.31 + 9.65(1H, s + d) |
| A-82 | 1H-NMR(CDCl3)δppm: 1.19-1.28(6H, m), 2.81(2H, q), 3.74(2H, s), 5.38(2H, s), 7.31(2H, d), 7.39(1H, d), 7.48(2H, d), 7.56(1H, d), 8.73(1H, s) |
| A-83 | 1H-NMR(CDCl3)δppm: 1.20(3H, t), 1.43(3H, t), 3.31-3.40(1H, m), 3.43-3.52(1H, m), 3.61(1H, s), 3.70(1H, s), |

TABLE 2-continued

| Compound No. | 1H-NMR [CDCl3/TMS, 400 MHz] |
|---|---|
| | 5.29(1H, s), 5.71(1H, br), 7.34(2H, s), 7.46(2H, s), 7.63(2H, d), 9.72 (1H, s) |
| A-84*[1] | 1H-NMR(CDCl3)δppm: 1.19-1.28 + 1.37(6H, m + t), 3.61 + 3.85(4H, q + d), 5.17 + 5.38(2H, s + s), 7.43-8.06(6H, m), 9.27(1H, s) |
| A-85*[1] | 1H-NMR(CDCl3)δppm: 1.19 + 1.28(6H, m), 2.83(2H, q), 3.71(2H, s), 5.37(2H, s), 7.39-7.45(3H, m), 7.62 + 7.66(3H, m), 8.77(1H, s) |
| A88 | 1H-NMR(CDCl3)δppm: 1.19-1.28(6H, m), 2.81(2H, q), 3.73(2H, s), 5.39(2H, s), 7.40-7.58(6H, m), 8.76(1H, s) |
| A-89 | 1H-NMR(CDCl3)δppm: 1.23(3H, t), 1.43(3H, t), 3.31-3.40(1H, m), 3.43-3.52(1H, m), 3.61(1H, s), 3.71(1H, s), 5.28 (1H, s), 5.70(1H, br), 7.44-7.61(6H, m), 9.74(1H, s) |
| A-90*[1] | 1H-NMR(CDCl3)δppm: 1.13 + 1.29 + 1.37(6H, s + s + t), 3.62 + 3.86(4H, d + d), 5.17 + 5.39(2H, s + s), 7.42-8.06(6H, m), 9.29(1H, s) |

*[1] a mixture of rotational isomers A and B at a ratio of about 5:1.

Formulations containing the compound of the present invention will now be specifically described with reference to some formulation examples, but the compound of the present invention, auxiliary ingredients, and the amounts thereof are not limited to those in the following Formulation Examples. Incidentally, the term "part(s)" in the following Formulation Examples means part(s) by mass.

Formulation Example 1: Emulsion Agent

The compound (10 parts) of the present invention, xylene (60 parts), N-methyl-2-pyrrolidone (20 parts), and Sorpol 3005X (the trade name of a mixture of a nonionic surfactant and an anionic surfactant available from TOHO Chemical Industry Co., Ltd.) (10 parts) were uniformly mixed and dissolved to obtain an emulsion agent.

Formulation Example 2: Water Dispersible Powder-1

The compound (20 parts) of the present invention, Nipsil NS-K (the trade name of white carbon available from Tosoh Silica Corporation) (10 parts), Kaolin Clay (the trade name of kaolinite available from Takehara Kagaku Kogyo Co., Ltd.) (60 parts), SAN X P-252 (the trade name of sodium lignin sulfonate available from NIPPON PAPER Chemicals Co., Ltd.) (5 parts), and Runox P-65L (the trade name of alkyl allyl sulfonate available from TOHO Chemical Industry Co., Ltd.) (5 parts) were uniformly mixed and pulverized in an air mill to obtain a water dispersible powder.

Formulation Example 3: Water Dispersible Powder-2

The compound (20 parts) of the present invention, Nipsil NS-K (the trade name of white carbon available from Tosoh Silica Corporation) (20 parts), Kaolin Clay (50 parts), Runox 1000C (the trade name of a naphthalene sulfonate condensate available from TOHO Chemical Industry Co., Ltd.) (5 parts), and Sorpol 5276 (the trade name of a nonionic surfactant available from TOHO Chemical Industry Co., Ltd.) (5 parts) were uniformly mixed and pulverized in an air mill to obtain a water dispersible powder.

Formulation Example 4: Water Soluble Agent-1

The compound (20 parts) of the present invention, Runox P-65L (the trade name of alkyl allyl sulfonate available from TOHO Chemical Industry Co., Ltd.) (3 parts), and a water-soluble carrier (potassium chloride) (77 parts) were uniformly mixed and pulverized to obtain a watersoluble agent.

Formulation Example 5: Water Soluble Agent-2

The compound (50 parts) of the present invention, Newkalgen BX-C (the trade name of sodium alkylnaphthalenesulfonate manufactured by TAKEMOTO OIL & FAT Co., Ltd.) (5 parts), silicon dioxide (2 parts), and a water-soluble carrier (43 parts) were uniformly mixed and pulverized to obtain a watersoluble agent.

Formulation Example 6: Flowable Agent-1

The compound (20 parts) of the present invention was dispersed in a mixed solution prepared in advance by mixing propylene glycol (5 parts), Sorpol 7933 (the trade name of an anionic surfactant available from TOHO Chemical Industry Co., Ltd.) (5 parts), and water (50 parts) to obtain a slurry-like mixture, this slurry-like mixture was then wet-pulverized with DYNO-MILL (Shinmaru Enterprise Corporation), and a dispersion prepared in advance by thoroughly mixing xanthan gum (0.2 parts) with water (19.8 parts) was added to the mixture to obtain a flowable agent.

Formulation Example 7: Flowable Agent-2

The compound (20 parts) of the present invention, Newkalgen FS-26 (the trade name of a mixture of dioctyl sulfosuccinate and polyoxyethylene tristyrylphenyl ether available from TAKEMOTO OIL & FAT Co., Ltd.) (5 parts), propylene glycol (8 parts), and water (50 parts) were mixed in advance, and this slurry-like mixture was wet-pulverized with DYNO-MILL (Shinmaru Enterprise Corporation). Subsequently, xanthan gum (0.2 parts) was thoroughly mixed with and dispersed in water (16.8 parts) to produce a gel-like substance and was sufficiently mixed with the pulverized slurry to obtain a flowable agent.

Formulation Example 8: EW-1

The compound (20 parts) of the present invention, Sorpol CA-42 (the trade name of a nonionic surfactant available from TOHO Chemical Industry Co., Ltd.) (15 parts), and preservative Proxel GX-L (0.1 parts) were mixed to be uniform, and water (59.6 parts) was then gradually added thereto with stirring to obtain a dispersion. An antifoam agent Antifoam E-20 (the trade name of emulsion-type modified silicone available from Kao Corporation) (0.1 parts) was added to the resulting dispersion, and xanthan gum (0.2 parts) dispersed in propylene glycol (5.0 parts) was added thereto to obtain an emulsion (phase inversion emulsification).

Formulation Example 9: EW-2

The compound (10 parts) of the present invention was dissolved in xylene (10 parts) and was mixed with a surfactant Rheodol 430V (the trade name of polyoxyethylene sorbitol tetraoleate available from Kao Corporation) (24 parts). The resulting mixed solution, an antifoam agent Antifoam E-20 (the trade name of an emulsion-type modified silicone system available from Kao Corporation) (0.1 parts), and a preservative Proxel GX-L (0.1 parts) were added to water (50.6 parts), followed by dispersing with a homogenizer. Xanthan gum (0.2 parts) dispersed in propylene glycol (5.0 parts) was added thereto to obtain an emulsion (mechanical emulsification).

Formulation Example 10: ME Agent-1

The compound (0.01 parts) of the present invention and Sorpol CA-42 (the trade name of a nonionic surfactant available from TOHO Chemical Industry Co., Ltd.) (0.1 parts) were mixed to be uniform, and water (99.79 parts) was then gradually added thereto with stirring. A preservative Proxel GX-L (0.1 parts) was added to the resulting dispersion to obtain a microemulsion.

Formulation Example 11: ME Agent-2

The compound (10 parts) of the present invention and Newkalgen D-945 (the trade name of polyoxyethylene (20 moles) sorbitan monooleate available from TAKEMOTO OIL & FAT Co., Ltd.) (20 parts) were mixed to be uniform, and water (69.9 parts) was then gradually added thereto with stirring. A preservative Proxel GX-L (0.1 parts) was added to the resulting dispersion to obtain a microemulsion.

Formulation Example 12: ME Agent-3

The compound (0.01 parts) of the present invention was dissolved in a solvent SOLVESSO 200 (0.08 parts) and Newkalgen ST-30 (the trade name of a mixture of polyoxyethylene arylphenyl ether formaldehyde condensate, a polyoxyalkylene arylphenyl ether, an alkylbenzene sulfonate, and xylene available from TAKEMOTO OIL & FAT Co., Ltd.) (0.12 parts) to be uniform, and water (99.69 parts) was gradually added thereto with stirring. A preservative Proxel GX-L (0.1 parts) was added to the resulting dispersion to obtain a microemulsion.

Formulation Example 13: Granule-1

The compound (5 parts) of the present invention, bentonite (30 parts), clay (60 parts), and sodium lignin sulfonate (5 parts) were uniformly mixed and pulverized, and water was added thereto, followed by thoroughly kneading. Then, extruding granulation and drying and sizing were performed to obtain granules.

Formulation Example 14: Granule-2

Silica sand (90 parts) was put in an oscillating granulator and was hydrated, and the compound (5 parts) of the present invention, sodium lignin sulfonate (4 parts), polyvinyl alcohol (PVA) (0.5 parts), and white carbon (0.5 parts) that were mixed and pulverized in advance were then put in the granulator for coating. Drying and sizing were then performed to obtain granules.

Formulation Example 15: Granule-3

Ishikawalite (89 parts) was put in an oscillating granulator and was hydrated, and the compound (5 parts) of the present invention, sodium lignin sulfonate (3 parts), sodium dioctyl sulfosuccinate (0.5 parts), POE styrylphenyl ether (2 parts), and polyvinyl alcohol (PVA) (0.5 parts) that were mixed and pulverized in advance were then put in the granulator for coating. Drying and sizing were then performed to obtain granules.

Formulation Example 16: Fine Granule-1

The compound (2 parts) of the present invention was diluted with a solvent and was mixed with pumice (98 parts) as a bulking agent by spraying the diluted solution. The resulting granular composition was dried, followed by sieving to obtain fine granules.

Formulation Example 17: Fine Granule-2

The compound (5 parts) of the present invention was air milled or mechanochemically ground as needed. This powdery source material and silica sand (85 parts) as a bulking agent were uniformly mixed, and the mixture was then mixed with a binder Toxanone GR-31A (10 parts) diluted with a solvent by spraying the diluted binder. The resulting granular composition was dried, followed by sieving to obtain fine granules.

Formulation Example 18: Powder Formulation

The compound (5 parts) of the present invention was uniformly mixed with white carbon (5 parts) and Clay (trade name, Nippon Talc Co., Ltd.) (90 parts), followed by pulverization to obtain a powder formulation.

Formulation Example 19: DL Powder Formulation

The compound (5 parts) of the present invention was uniformly mixed with propylene glycol (0.5 parts) and DL Clay (94.5 parts), followed by pulverization to obtain a powder formulation.

Formulation Example 20: Seed Coating Powder Formulation

The compound (10 parts) of the present invention, sodium lignin sulfonate (6 parts), polyvinyl alcohol (PVA) (1 part), and Clay (trade name, Nippon Talc Co., Ltd.) (83 parts) were uniformly mixed and pulverized to prepare a powder formulation. The powder formulation was mixed with pre-moistened seeds, followed by air drying to obtain coated seeds.

The effect and usefulness of the compound of the present invention will be described with specific examples. The compounds of the present invention are indicated by the compound numbers shown in Table 1, and the compounds used as comparison controls are indicated by the following compound formulae.

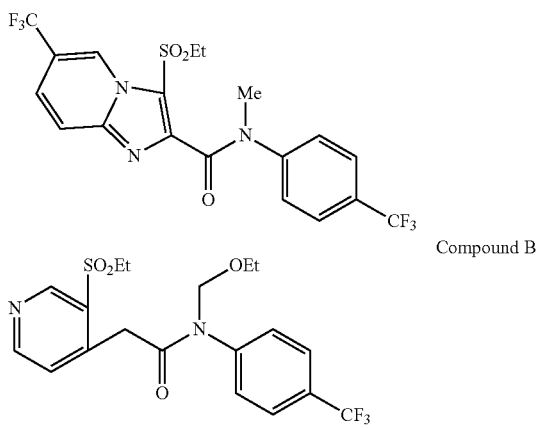

Compound A

Compound B

Test Example 1: Insecticidal Effect Test for *Plutella xylostella* of Chinese Cabbage A sufficient amount of a water diluted solution of an emulsion agent (500 ppm) prepared as in Formulation Example 1 was sprayed with an air brush to the leaves of Chinese cabbage seedlings planted in pots raised for 2 weeks after sowing. The liquid agent was air dried, and five 3rd instar larvae of *Plutella xylostella* were then inoculated per pot and were kept in a thermostat chamber of 25° C. Five days after the insect release, the life-and-death and the agony of the larvae were investigated, and the insecticidal rate (%) when agony insects were included in dead insects was determined. Incidentally, the test was carried out by using one seedling in each ward.

Insecticidal rate (%)=[number of dead larvae)/(number of test larvae)]×100

As a result, for the present Compound Nos. A-13, A-14, A-15, A-18, A-20, A-21, A-22, A-25, A-27, A-31, A-33, A-70, A-72, A-75, A-91, A-96, A-99, and A-102, the insecticidal rate was 100%. In contrast, the insecticidal rates of Compound A and Compound B were 90% and 50%, respectively.

Test Example 2: Larvicide test for *Spodoptera litura* (Fabricius)

A water diluted solution of an emulsion agent (500 ppm) prepared as in Formulation Example 1 was put in a 120-mL polyethylene cup, and artificial feed Insecta LF (Nosan Corporation, diameter: 5 cm) sliced into 5 mm thickness and cut into ¼ was immersed in the polyethylene cup for about 60 seconds. After the immersion treatment, the resultant artificial feed piece was put in another 120-mL polyethylene cup (diameter: 8 cm, height: 4 cm) with filter paper (diameter: 55 mm) on the bottom together with test insects, and the cup was covered with a lid and was then kept in a thermostat chamber of 25° C. Seven days after the insect release, the life-and-death and the agony of the larvae were investigated, and the insecticidal rate (%) when agony insects were included in dead insects was determined. Incidentally, the test was carried out by using one cup in each ward.

Insecticidal rate (%)=[number of dead larvae)/(number of test larvae)]×100

As a result, for the present Compound Nos. A-13, A-14, A-15, A-18, A-20, A-21, A-22, A-25, A-27, A-33, A-70, A-72, A-75, A-91, A-96, A-99, and A-102, the insecticidal rate was 100%. In contrast, the insecticidal rates of Compound A and Compound B were 90% and 0%, respectively.

Test Example 3: Adult-Killing Test for *Aculops lycopersici* Massee

A lid provided with a hole (diameter: about 5 mm) at the center was put on a 430-mL polyethylene cup containing water. Circular filter paper with a diameter of 6.5 cm which was cut such that a strip-shaped filter paper piece having a width of about 5 mm was formed was put on the lid, and the filter paper piece was inserted into the hole of the lid so that the tip of the piece extends downward from the hole and immersed in the water in the cup. Furthermore, absorbent cotton was put on the filter paper such that the water in the cup was always supplied to the absorbent cotton. Three leaf disks (1 cm×1 cm) of leaflets of tomato in the early stage of true leaf development were put on the absorbent cotton such that the back of the leaves in the disk form was on top, and small pieces of a leaf parasitized by tomato rust mites were inoculated on the leaves in the disk form. After 24 hours from the inoculation, the small pieces were removed, and the cup was placed in an acrylic cylinder having a height of 50 cm and a diameter of 10 cm. A water diluted solution of an emulsion agent (500 ppm) prepared as in Formulation Example 1 was sprayed in an amount of 2.0 mL per cup using an air brush. After the spraying, the cup was kept in a thermostat chamber of 25° C. Three days after the treatment, the control rate was evaluated on four scales: 100 (control rate: 100%), 80 (control rate: 99% to 80%), 50 (control rate: 79% to 50%), and 0 (control rate: less than 50%), and the next-generation density suppression rate was calculated based on the results by the following equation. Incidentally, the test was carried out by using one cup in each ward.

Control rate=($A$×100+$B$×80+$C$×50)/($A$+$B$+$C$+$D$)

A: the number of disks for 100, B: the number for disks of 80, C: the number for disks of 50, D: the number of disks for 0.

As a result, for the present Compound Nos. A-14, A-15, A-25, A-27, A-33, A-70, A-72, A-75, A-96, and A-102, the control rate was 100%. The control rates of Compound A and Compound B were both 100%.

The invention claimed is:
1. An imidazopyridine-2-carboxamide derivative represented by a following formula (1), or its N-oxide or salt:

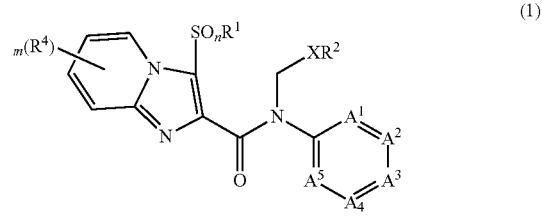

wherein: $R^1$ represents a $C_{1-6}$ alkyl group or a $C_{1-6}$ haloalkyl group;
$R^2$ represents a hydrogen atom, a $C_{1-6}$ alkyl group, or a $C_{1-6}$ haloalkyl group;
X represents an oxygen atom, a sulfur atom, or —$SO_2$—;

A¹, A², A³, A⁴, and A⁵ each independently represents a nitrogen atom or C—R³, wherein two of A¹, A², A³, A⁴, and A⁵ are not nitrogen atoms at the same time, and at least one of A¹, A², A³, A⁴, and A⁵ is C—R³;

R³s are the same or different from each other, and each R³ represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a $C_{3-6}$ alkenyloxy group, a $C_{3-6}$ alkynyloxy group, a $C_{1-6}$ haloalkoxy group, a $C_{3-6}$ haloalkenyloxy group, a $C_{3-6}$ haloalkynyloxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a nitro group, a cyano group, a phenyl group optionally substituted with one to four R⁵s, a phenoxy group optionally substituted with one to four R⁶s, or a triazolyl group substituted with one or two R⁷s, or when two R³s are substituted on adjacent two carbon atoms, the two R³s optionally form a saturated or unsaturated 5- or 6-membered ring together with the adjacent two carbon atoms to which the R³s are respectively bound, and R⁵, R⁶, and R⁷ each independently represents a halogen atom, a $C_{1-6}$ alkyl group, a $C_{1-6}$ haloalkyl group, a $C_{3-8}$ cycloalkyl group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, or a $C_{1-6}$ haloalkylsulfonyl group;

R⁴s are the same or different from each other and each represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a nitro group, or a cyano group;

n represents an integer of 0 to 2; and m represents an integer of 0 to 4.

2. The imidazopyridine-2-carboxamide derivative or its N-oxide or salt according to claim 1, wherein R¹ represents a $C_{1-6}$ alkyl group.

3. The imidazopyridine-2-carboxamide derivative or its N-oxide or salt according to claim 1, wherein R² represents a $C_{1-6}$ alkyl group.

4. The imidazopyridine-2-carboxamide derivative or its N-oxide or salt according to claim 1, wherein X represents an oxygen atom.

5. The imidazopyridine-2-carboxamide derivative or its N-oxide or salt according to claim 1, wherein X represents a sulfur atom.

6. The imidazopyridine-2-carboxamide derivative or its N-oxide or salt according to claim 1, wherein
R¹ is a $C_{1-6}$ alkyl group, and
R² is a $C_{1-6}$ alkyl group.

7. The imidazopyridine-2-carboxamide derivative or its N-oxide or salt according to claim 1, wherein
R¹ is a $C_{1-6}$ alkyl group,
R² is a $C_{1-6}$ alkyl group, and
X is O.

8. The imidazopyridine-2-carboxamide derivative or its N-oxide or salt according to claim 1, wherein
R¹ is a $C_{1-6}$ alkyl group,
R² is a $C_{1-6}$ alkyl group, and
X is S.

9. The imidazopyridine-2-carboxamide derivative or its N-oxide or salt according to claim 1, wherein
R¹ is methyl, ethyl, or isopropyl,
R² is methyl or ethyl,
A¹, A², A³, A⁴, and A⁵ are independently CH, CF, $CC_2F_5$, $COCF_3$, $CSCF_3$, $CSOCF_3$, $CSO_2F_3$, $CSC_2F_5$, $CSF_5$, $CCF(CF_3)_2$, CCl, CBr, CCN, $CNO_2$, CMe, or $CCF_3$,
X is O or S, and
R⁶ is 6-$CF_3$.

10. The imidazopyridine-2-carboxamide derivative or its N-oxide or salt according to claim 1, wherein
R¹ is methyl, ethyl, or isopropyl,
R² is methyl or ethyl,
A¹, A², A³, A⁴, and A⁵ are independently CH or $CCF_3$, and
X is O.

11. The imidazopyridine-2-carboxamide derivative or its N-oxide or salt according to claim 1, wherein
R¹ is methyl, ethyl, or isopropyl,
R² is methyl or ethyl,
A³ is $CCF_3$,
A¹, A², A⁴, and A⁵ are CH, and
X is O.

12. The imidazopyridine-2-carboxamide derivative or its N-oxide or salt according to claim 1, wherein
R¹ is methyl,
R² is methyl or ethyl,
A³ is $CCF_3$,
A¹, A², A⁴, and A⁵ are CH, and
X is O.

13. The imidazopyridine-2-carboxamide derivative or its N-oxide or salt according to claim 1, wherein
R¹ is ethyl,
R² is methyl or ethyl,
A³ is $CCF_3$,
A¹, A², A⁴, and A⁵ are CH, and
X is O.

14. The imidazopyridine-2-carboxamide derivative or its N-oxide or salt according to claim 1, wherein
R¹ is isopropyl,
R² is methyl or ethyl,
A³ is $CCF_3$,
A¹, A², A⁴, and A⁵ are CH, and
X is O.

15. The imidazopyridine-2-carboxamide derivative or its N-oxide or salt according to claim 1, wherein
R¹ is methyl, ethyl, or isopropyl,
R² is methyl,
A³ is $CCF_3$,
A¹, A², A⁴, and A⁵ are CH, and
X is O.

16. The imidazopyridine-2-carboxamide derivative or its N-oxide or salt according to claim 1, wherein
R¹ is methyl, ethyl, or isopropyl,
R² is ethyl,
A³ is $CCF_3$,
A¹, A², A⁴, and A⁵ are CH, and
X is O.

17. A method for manufacturing an imidazopyridine-2-carboxamide derivative of formula (1-1) or (1-2):
the method comprising oxidizing an imidazopyridine-2-carboxamide derivative of formula (1-0) to obtain the imidazopyridine-2-carboxamide derivative of formula (1-1) or (1-2):

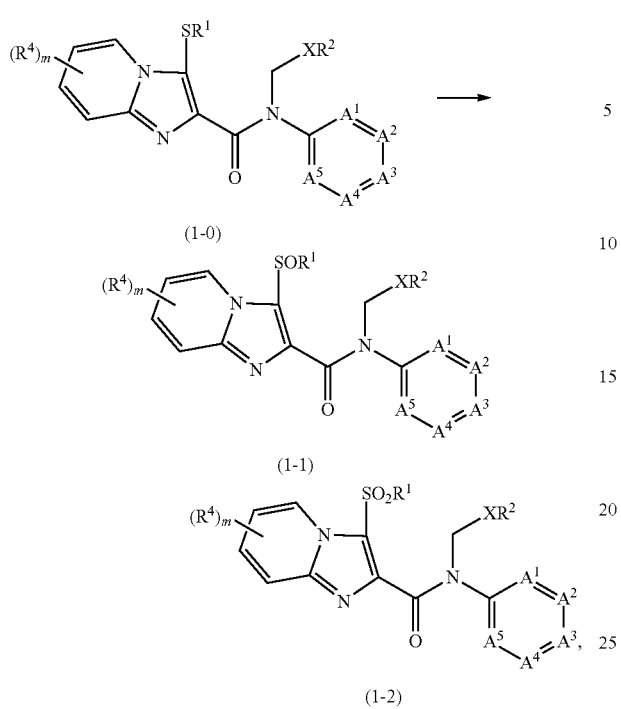

wherein:

$R^1$ represents a $C_{1-6}$ alkyl group or a $C_{1-6}$ haloalkyl group;

$R^2$ represents a hydrogen atom, a $C_{1-6}$ alkyl group, or a $C_{1-6}$ haloalkyl group;

X represents an oxygen atom, a sulfur atom, or —$SO_2$—;

$A^1$, $A^2$, $A^3$, $A^4$, and $A^5$ each independently represents a nitrogen atom or C—$R^3$, wherein two of $A^1$, $A^2$, $A^3$, $A^4$, and $A^5$ are not nitrogen atoms at the same time, and at least one of $A^1$, $A^2$, $A^3$, $A^4$, and $A^5$ is C—$R^3$;

$R^3$s are the same or different from each other, and each $R^3$ represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a $C_{3-6}$ alkenyloxy group, a $C_{3-6}$ alkynyloxy group, a $C_{1-6}$ haloalkoxy group, a $C_{3-6}$ haloalkenyloxy group, a $C_{3-6}$ haloalkynyloxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a nitro group, a cyano group, a phenyl group optionally substituted with one to four $R^5$s, a phenoxy group optionally substituted with one to four $R^6$s, or a triazolyl group substituted with one or two $R^7$s, or when two $R^3$s are substituted on adjacent two carbon atoms, the two $R^3$s optionally form a saturated or unsaturated 5- or 6-membered ring together with the adjacent two carbon atoms to which the $R^3$s are respectively bound, and $R^5$, $R^6$, and $R^7$ each independently represents a halogen atom, a $C_{1-6}$ alkyl group, a $C_{1-6}$ haloalkyl group, a $C_{3-8}$ cycloalkyl group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, or a $C_{1-6}$ haloalkylsulfonyl group;

$R^4$s are the same or different from each other and each represents a hydrogen atom, a halogen atom, a $C_{1-6}$ alkyl group, a $C_{1-6}$ haloalkyl group, a $C_{3-8}$ cycloalkyl group, a $C_{1-6}$ alkoxy group, a nitro group, or a cyano group;

n represents an integer of 0 to 2; and m represents an integer of 0 to 4.

18. A method for controlling plant harmful organisms, the method comprising:

treating harmful organisms and/or a habitat environment thereof and/or seeds as a target to be attached by harmful organisms and/or a plant breeding material with the imidazopyridine-2-carboxamide derivative or its N-oxide or salt according to claim 1, wherein the plant harmful organism is an insect or an acarid.

19. A method for controlling plant harmful organisms, the method comprising:

treating a place where a crop is allowed to grow or is growing or a growing crop with the imidazopyridine-2-carboxamide derivative or its N-oxide or salt according to claim 1, wherein the plant harmful organism is an insect or an acarid.

20. A method for preparing an agrochemical composition, the method comprising:

mixing the imidazopyridine-2-carboxamide derivative or its N-oxide or salt according to claim 1 with a bulking agent and/or a surfactant.

* * * * *